US006201394B1

(12) United States Patent
Danby et al.

(10) Patent No.: US 6,201,394 B1
(45) Date of Patent: *Mar. 13, 2001

(54) MRI APPARATUS

(75) Inventors: Gordon T. Danby, Wading River; John Linardos, Smithtown; Jevan Damadian, East Northport; Raymond V. Damadian, Woodbury, all of NY (US)

(73) Assignee: Fonar Corporation, Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/975,913

(22) Filed: Nov. 21, 1997

Related U.S. Application Data

(63) Continuation-in-part of application No. 07/993,072, filed on Dec. 18, 1992, now Pat. No. 6,023,165.

(51) Int. Cl.[7] ..................................................... G01V 3/00
(52) U.S. Cl. ................................... 324/319; 324/320
(58) Field of Search ................................... 324/319, 318, 324/320, 322, 300; 335/296, 216

(56) References Cited

U.S. PATENT DOCUMENTS

| D. 313,073 | 12/1990 | Kaufman et al. . |
| 4,490,675 | 12/1984 | Knuettel et al. . |
| 4,613,820 | 9/1986 | Edelstein et al. . |
| 4,629,989 | 12/1986 | Riehl et al. . |
| 4,641,119 | 2/1987 | Moore . |
| 4,644,275 | 2/1987 | Young . |
| 4,651,099 | 3/1987 | Vinegar et al. . |
| 4,672,346 | 6/1987 | Miyamoto et al. . |
| 4,679,022 | 7/1987 | Miyamoto et al. . |
| 4,691,163 | 9/1987 | Blass et al. . |
| 4,707,663 | 11/1987 | Minkoff et al. . |
| 4,766,378 | 8/1988 | Danby et al. . |
| 4,777,464 | 10/1988 | Takabatashi et al. . |
| 4,829,252 | 5/1989 | Kaufman . |
| 4,924,198 | 5/1990 | Laskaris . |
| 4,943,774 | 7/1990 | Breneman et al. . |
| 4,968,937 | 11/1990 | Akgun . |
| 4,989,608 | 2/1991 | Ratner . |
| 5,124,651 | 6/1992 | Danby et al. . |
| 5,134,374 | 7/1992 | Breneman et al. . |
| 5,153,546 | 10/1992 | Laskaris . |
| 5,194,810 | 3/1993 | Breneman et al. . |
| 5,197,474 | 3/1993 | Englund et al. . |
| 5,207,224 | 5/1993 | Dickinson et al. . |
| 5,211,165 | 5/1993 | Dumoulin et al. . |
| 5,229,723 | 7/1993 | Sakurai et al. . |
| 5,250,901 | 10/1993 | Kaufman et al. . |
| 5,290,266 | 3/1994 | Rohling et al. . |
| 5,304,932 | 4/1994 | Carlson . |
| 5,305,749 | 4/1994 | Li et al. . |
| 5,315,276 | 5/1994 | Huson et al. . |
| 5,382,905 | 1/1995 | Miyata et al. . |
| 5,412,363 | 5/1995 | Breneman et al. . |

FOREIGN PATENT DOCUMENTS 62-26052    2/1987   (JP) .

Primary Examiner—Louis Arana
(74) Attorney, Agent, or Firm—Lerner, David, Littenberg, Krumholz & Mentlik, LLP

(57) ABSTRACT

A magnet for magnetic resonance imaging has an interior working space within the magnet frame sufficient to accommodate a physician and a patient. Because the physician is positioned inside the magnet frame, the physician has unimpeded access to the patient. Elements of the magnet frame desirably encompass a room, and the magnet frame may be concealed from view of a patient within the room. Preferred embodiments facilitate MRI imaged guided surgery and other procedures performed while the patient is being imaged, and minimize claustrophobia experienced by the patient.

73 Claims, 14 Drawing Sheets

U.S. PATENT DOCUMENTS

| | | |
|---|---|---|
| 5,436,607 | 7/1995 | Chari et al. . |
| 5,490,513 | 2/1996 | Damadian et al. . |
| 5,519,372 | 5/1996 | Palkovich et al. . |
| 5,754,085 | 5/1998 | Danby et al. . |
| 5,917,395 * | 6/1999 | Overweg ................................ 335/296 |
| 6,023,165 * | 2/2000 | Damadian et al. ................... 324/318 |

* cited by examiner

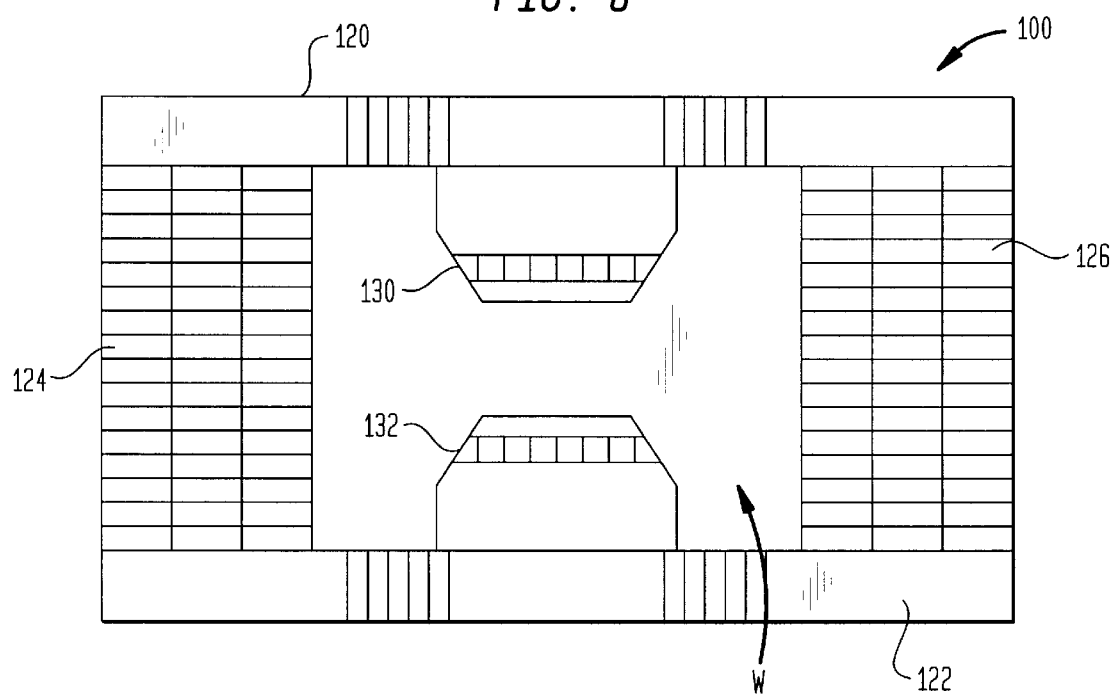

MRI APPARATUS

CROSS REFERENCE TO RELATED APPLICATION

The present application is a continuation-in-part of U.S. patent application Ser. No. 07/993,072, filed Dec. 18, 1992, now U.S. Pat. No. 6,023,165 the disclosure of which is hereby incorporated by reference herein.

BACKGROUND OF THE INVENTION

The present invention relates to magnetic resonance imaging or "MRI".

MRI is widely used in medical and other arts to obtain images of a subject such as a medical patient. The patient's body is placed within a subject receiving space of a primary field magnet and exposed to a strong, substantially constant primary magnetic field. The atomic nuclei spin around axes aligned with the magnetic field. Powerful radio frequency "RF" signals are broadcast into the subject receiving space to excite atomic nuclei within the patient's body into a resonance state in which the spinning nuclei generate minuscule RF signals, referred to herein as magnetic resonance signals. By applying magnetic field gradients so that the magnitude of the magnetic field varies with location inside the subject-receiving space characteristics of the magnetic resonance signals from different locations within the region, such as the frequency and phase of the signals, can be made to vary in a predictable manner depending upon position within the region. Thus, the magnetic resonance signals are "spatially encoded" so that it is possible to distinguish between signals from different parts of the region. After repeating this procedure with various different gradients, it is possible to derive a map showing the intensity or other characteristics of the magnetic resonance signals versus position within the excited region. Because these characteristics vary with concentration of different chemical substances and other characteristics of the tissue within the subject's body, different tissues provide different magnetic resonance signal characteristics. When the map of the magnetic resonance signal characteristics is displayed in a visual format, such as on screen or on a printed image, the map forms a visible picture of structures within the patient's body.

MRI provides unique imaging capabilities which are not attainable in any other imaging method. For example, MRI can provide vivid, detailed images of soft tissue abnormal tissues such as tumors, and other structures which cannot be seen readily in X-ray images. Moreover, MRI operates without exposing the patient to ionizing radiation such as X-rays. For these and other reasons, MRI is widely utilized in medicine.

Some of the primary field magnets utilized heretofore have imposed severe physical constraints on the patient and on medical personnel attending to the patient during the MRI procedure. For example, conventional solenoidal primary field magnets use a series of circular super-conducting coils spaced apart from one another along an axis. These magnets provide a small, tubular subject-receiving space enclosed within the solenoids. A patient to be imaged must slide into the tubular space. The experience is highly claustrophobic. Some obese or pregnant patients often cannot fit inside the patient-receiving space. Moreover, it is essentially impossible for a physician to reach those regions of the patient disposed inside the subject receiving space.

Attempts have been made heretofore to create "open" MRI primary field magnets using ferromagnetic frames. Although these designs provide somewhat better access to the patient for diagnostic scanning, and a somewhat less claustrophobic experience for the patient, they are less than optimal for surgical intervention. For example, these designs provide limited access of physicians and surgeons to the patient. Additionally, the designs have difficulty providing a highly uniform field with pole dimensions desirable for surgery.

As described, for example, in commonly assigned U.S. Pat. No. 4,707,663, other primary field magnets utilize ferromagnetic frames to route and concentrate magnetic flux into the patient receiving space. Primary field magnets using such a ferromagnetic frame can employ permanent magnets, resistive electromagnetic coils, or super-conducting coils having a relatively low number of ampere terms while still providing a high field strength in the patient-receiving space. Moreover, such magnet assemblies can provide excellent field uniformity. Ferromagnetic frame magnets in accordance with the '663 patent also provide a less claustrophobic, more accessible subject receiving space.

As disclosed in co-pending, commonly assigned U.S. patent application Ser. No. 07/952,810 filed Sep. 28, 1992, the disclosure of which is hereby incorporated by reference herein, a ferromagnetic magnetic frame may include a pair of plate-like pole supports spaced apart from one another and supported above one another by a set of columns. In preferred magnets according to '810 application, the frame defines a polar axis passing through the space between the plates. Preferably, ferromagnetic poles project from the pole supports adjacent the polar axis, so that the poles define a subject receiving spacing at a medial plane, midway between the plates. The columns have unique shapes such that, in preferred embodiments, the columns flare outwardly in the radial direction, away from the polar axis adjacent the medial plane. The dimensions of each column in the circumferential direction, around the polar axis desirably taper so that the circumferential dimension of each column is at a minimum in a region adjacent the medial plane. As described in further detail in the '810 application, magnets with ferromagnetic frames in accordance with preferred embodiments of the invention taught therein can provide a unique combination of accessibility and a large, aesthetically pleasing and non-claustrophobic patient-receiving space and can also provide high field strength without resort to super-conducting coils. Even higher field strengths can be provided where superconducting coils are used. Magnets according to preferred embodiments taught in the '810 application thus provide an elegant solution to the problems of claustrophobia, lack of access and limitations on field strength and uniformity posed by prior designs. Surgical operations and other medical procedures can be performed readily on a patient while the patient is disposed inside the patient-receiving space of preferred magnets according the '810 application. The ability to perform surgical operations while the patient is disposed inside the patient-receiving space allows the physician to treat the patient under direct guidance of a MRI image acquired during the procedure itself. For example, as the surgeon advances a probe into the body to treat a lesion, the surgeon can see the probe and the lesion in the MRI image.

However, even with this enhanced design, the patient still perceives the MRI procedure as involving placement of his or her body into the interior of a machine. Moreover, the physician treating the patient still perceives that he or she must stand outside of the apparatus and reach into the apparatus to gain access to the patient. Accordingly, even further improvement in primary field magnet structures for MRI apparatus would be desirable.

SUMMARY OF THE INVENTION

One aspect of the present invention provides a magnet for magnetic resonance imaging apparatus which includes a frame. The frame desirably incorporates a pair of opposed ferromagnetic pole supports spaced apart from one another and a pair of ferromagnetic poles connected to the pole support. The poles project from the pole supports toward one another along a polar axis. The poles have distal ends remote from the pole supports. The distal ends confront one another and are spaced apart from one another by a gap distance so as to define a subject-receiving gap between the poles. The frame further includes one or more connecting elements extending between the pole supports. The connecting elements are spaced apart from the poles in a direction or directions transverse to the polar axis. The magnet further includes a source of magnetic flux adapted to direct flux through the frame so that the flux passes between the distal ends of the poles through the gap and returns through the pole supports and the connecting elements.

Most preferably, the magnet defines a working space alongside of the poles, between the pole supports and the poles and between the connecting elements sufficient to accommodate one or more adult human attendants. Thus, an attendant can be positioned inside the working space, within the magnet itself and can have access to a patient disposed in the gap between the poles. The working space desirably is about six feet or more high and about two feet or more wide, so that the attendant can work in a standing position. Most preferably, the working space extends entirely around the poles, and is unobstructed by any feature of the magnet itself. The magnet desirably includes a plurality of enclosing structures including walls, a floor and a ceiling which cooperatively define a room. The poles extend into the room, but the remainder of the frame desirably is at or outside the exterior of the room. For example, where the pole supports are spaced vertically apart from one another and the polar axis extends vertically, the poles project into the room from the floor and ceiling. Thus, the patient experiences entry into the MRI magnet as entry into a normal room with some structures extending from the floor and ceiling. Stated another way, the elements such as the connecting elements and pole supports are so far away from the patient that they do not create any feeling of claustrophobia. Because the physician or other attendant is inside the room and inside the space enclosed by the pole supports and connecting elements, these elements do not impede access by the physician to the patient at all. The connecting elements may be in the form of plates constituting one or more walls of the room as well as providing the pole supports which may be formed as further plates constituting the floor and ceiling of the room. The enclosing structure may further include concealment structure which conceals those parts of the frame constituting the walls from view from within the room. For example, the interior surfaces of the plates may be covered with conventional wall, floor and ceiling coverings. This contributes to the patient's belief that he or she is inside a normal room.

Because the pole supports and connecting elements are disposed outside of the area occupied by the patient and attendant, these elements can be of essentially unlimited size. Essentially any amount of ferromagnetic material can be used to provide a low reluctance flux return path and to perform uniform distribution of flux passing to the poles. Magnets in accordance with preferred aspects of the present invention thus can provide a highly concentrated, strong magnetic field in the subject receiving gap. Magnets according to this aspect of the invention can utilize permanent magnets, super-conducting coil or, resistive electromagnetic coils as the source of electromagnetic flux. In a particularly preferred arrangement, a coil such as a resistive electromagnetic coil encircles each pole. Thus, the working space extends around the poles between the coils. Where the polar axis extends vertically, the working space desirably extends above one coil and below the other coil.

The gap distance between the distal ends of the pole preferably is about two feet or more and most preferably at least about three feet so as to provide an extraordinarily open, non-claustrophobic space for the patient and excellent access for the physician. In a particularly preferred arrangement, the gap distance is between about 3 feet and about 4 feet. The distal ends of the poles may be either circular or non-circular. Where the distal ends of the poles are circular, the ratio between the diameter of each pole distal end and the gap distance between the poles is desirably less than about 2 to 1. Where the distal ends of the poles are noncircular, the ratio between the longest dimension of each pole surface and the gap distance is also desirably less than about 2 to 1, and the ratio of the shortest dimension of each pole surface to the gap distance desirably is about 1.5:1 or less. The magnet desirably incorporates features to further enhance field uniformity in the patient receiving gap. Where coils are employed as the source of magnetic flux, each coil encircles the associated pole. Also, the magnet desirably includes shimming features such as shim rings, slots or other elements defining magnetic flux paths having different reluctances at different distances from the polar axis. To further promote field uniformity, each pole may include a pole tip defining a distal end of the pole and a pole stem extending from the proximal end of the pole to the pole tip. The flux source is arranged to direct the flux in a forward direction through each pole. The magnet may include stem bucking magnets surrounding the pole stem. The stem bucking magnets desirably provide flux directed in a reversed direction opposite to the forward direction. This tends to minimize leakage of flux from the pole stems to the connecting elements. The relatively large spacing between the poles and the connecting elements in radial directions transverse to the polar axis helps to minimize flux leakage from the poles, so that a very large portion of the flux tends to pass between the poles. This further promotes flux uniformity and a strong field in the subject receiving gap.

In a particularly preferred arrangement, the vertical connecting elements are disposed at least about 7 feet from the polar axis. Thus, a typical human patient can be positioned with the long axis of his or her body extending in any desired radial direction and with any portion of his or her body at the polar axis. For example, if the patient's head is positioned at the polar axis, as where procedures or imaging are to be performed on the head, the patient's feet can point in any direction. In one arrangement, the connecting elements include a pair of connecting elements such as a pair of opposed, heavy, plate-like walls disposed at least about 14 feet apart from one another and defining two opposite ends of a room. In other embodiments, the polar axis may extend horizontally, and the pole supports may extend along walls of the room defined by the magnet frame.

These and other objects, features and advantages of the present invention will be more readily apparent from the detailed description of the preferred embodiments set forth below, taken in conjunction with the accompanying drawings.

BRIEF DESCRIPTION OF TIE DRAWINGS

FIG. 6 is a view similar to FIG. 2 but depicting apparatus in accordance with a further embodiment of the invention.

DETAILED DESCRIPTION OF THE PREFERRED EMBODIMENTS

Figure 1:
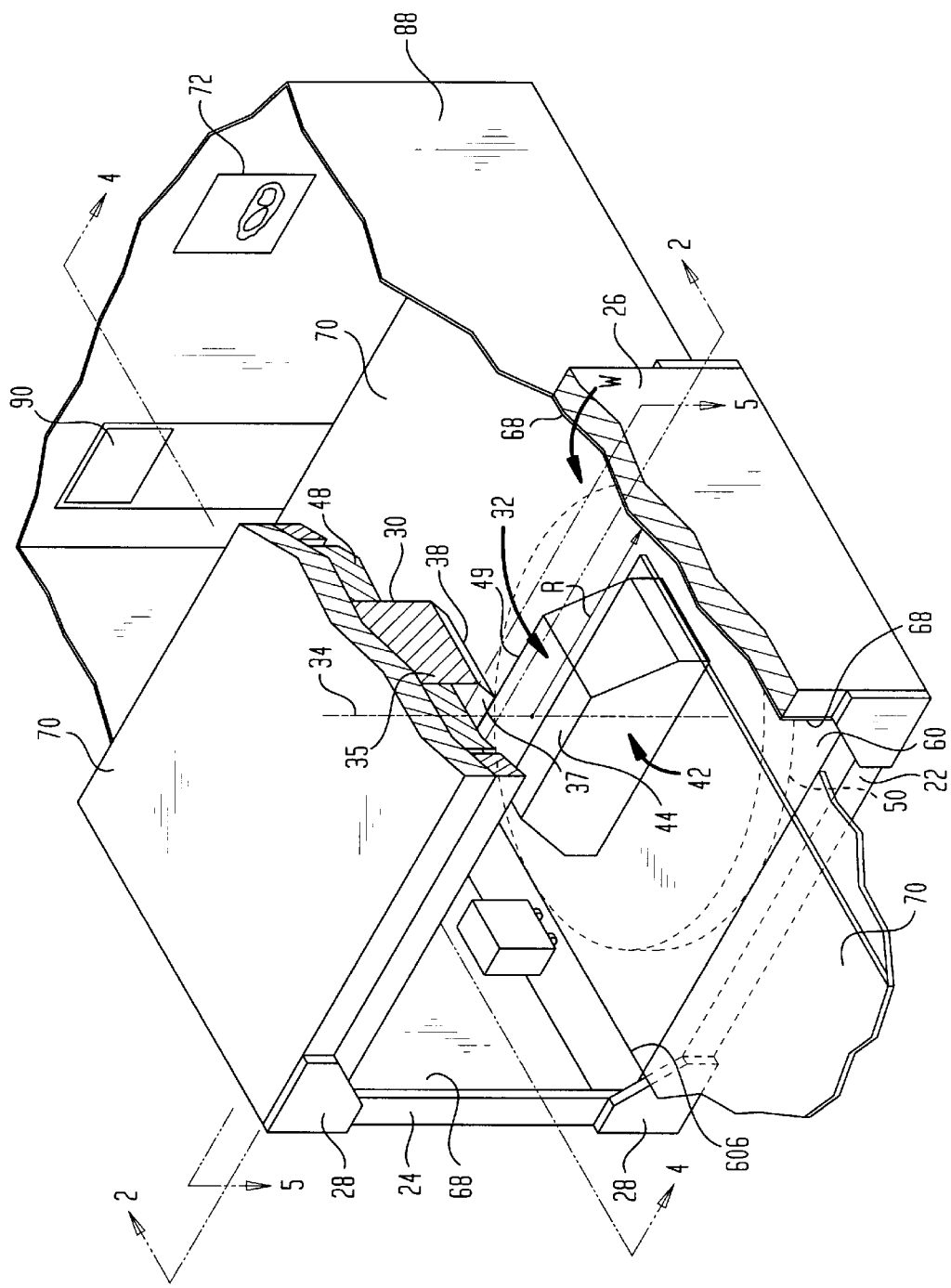
FIG. 1 is a diagrammatic perspective view depicting elements of apparatus in accordance with one embodiment of the invention.

Apparatus in accordance with one embodiment of the invention (FIG. 1) includes an upper pole support 20 and a lower pole support 22. Each of these pole supports includes a steel slab approximately sixteen feet long, ten feet wide, and about twelve inches thick. The upper pole support is held above the lower pole support by a pair of connecting elements 24 and 26. Each of the connecting elements is a steel slab approximately nine feet tall, ten feet wide, and 12 inches thick. Ferromagnetic connecting elements 24 and 26 are disposed between the pole supports at the ends thereof, so that the upper pole support lies approximately eleven feet above the lower pole support and so that the inwardly facing surfaces of the connecting elements are spaced apart from one another by a distance of approximately fourteen feet. As best appreciated with reference to FIG. 1, the pole supports 20 and 22 and the connecting elements 24 and 26 form four sides of a rectangular box. Elements 20, 22, 24 and 26 in combination provide the flux return path. Gusset plates 28 are provided at the corners of the box to reinforce it against racking and twisting stresses.

Figure 2:
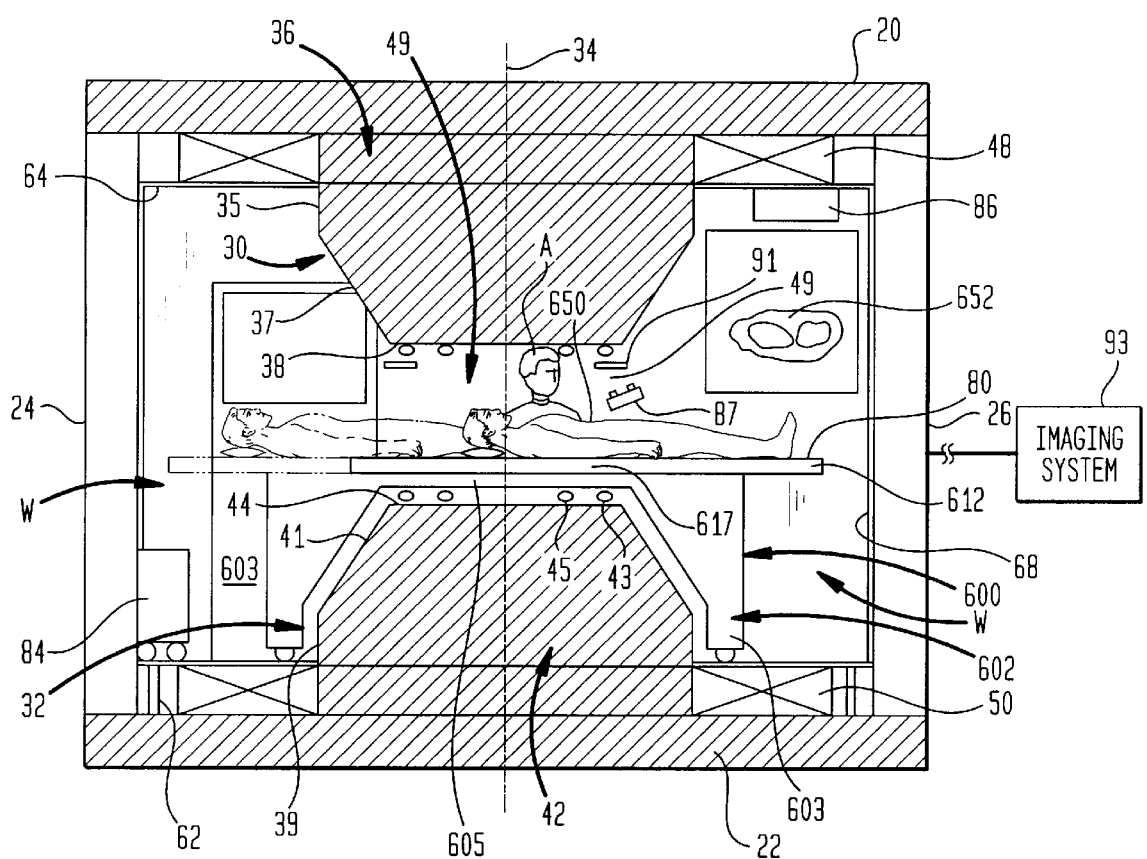
FIG. 2 is a diagrammatic sectional elevational view taken along line 2—2 in FIG. 1.

An upper ferromagnetic pole 30 projects downwardly from upper pole support 20, whereas a lower ferromagnetic pole 32 projects upwardly from the lower pole support 22. Poles 30 and 32 are generally in the form of rectangular solids. As best seen in FIG. 2, the upper pole 30 includes a ferromagnetic pole stem 36 extending from the upper pole support, a generally rectangular pole tip 38 disposed at the distal end of the pole remote from the pole support. The pole stem 36 includes a proximal portion 35 of substantially uniform cross-sectional shape adjacent the pole support, and a tapering portion 37 having a progressively smaller long dimension in the distal direction away from the pole support. The short dimension of the pole stem remains constant from the pole support to tip 38. The lower pole 32 has a similar pole stem 42, with uniform portion 39 at the proximal end of the pole and tapering portion 41 tapering inwardly in the distal direction toward the pole tip 44. The taper or progressive reduction in the long dimension of the poles minimizes saturation in the pole stem and aids in providing a uniform field even with relatively narrow poles having a small short dimension. The narrow poles provide better access to the patient for the physician or surgeon. As best seen in FIGS. 5A–5D, the proximal portion 39 of the lower pole stem has rounded corners. The proximal portion 35 of the upper pole stem has similar rounded corners. Both poles are aligned with one another and define a polar axis 34 extending vertically, transverse to pole supports 20 and 22, through the centers of the poles. The long dimensions of the poles are aligned with one another so as to provide an elongated patient receiving gap 49 between the poles. The pole tips desirably have a ratio of long dimension to short dimension of about 4:3 or more, and more preferably about 1.5:1. For example, the pole tips may have dimensions of about 48 inches (1.22 m) by about 72 inches, whereas the pole stem bases may also be generally rectangular and may have dimensions of about 48 inches (1.22 m) by about 86 inches (2.18 m). The distance between pole tips 38 and 44 and hence the dimension of gap 49 in the axial direction along polar axis 34 desirably is at least about 17.5 inches and more desirably about 36 inches. The ratio between the shortest dimensions of the pole tips and the dimension of the gap in the axial direction is most preferably about 1.3:1. This ratio desirably is about 1:1 and about 2:1 or less.

A resistive electromagnet coil 48 encircles the stem 36 of upper pole 30 at its juncture with the upper pole support 20. A corresponding lower resistive electromagnetic coil 50 encircles the stem 42 of the lower pole at its juncture with lower pole support 22. The electromagnetic coils 48 and 50 are also generally rectangular in shape. In this example, each one of the coils may have a width M about 33 inches and a thickness in about 12 inches. This large area keeps resistive power losses low. For superconducting coils, this area will be greatly reduced.

The apparatus also includes the other components conventionally utilized in MRI apparatus. For example gradient coils 45 (FIG. 2)are disposed adjacent gap 49 for applying magnetic field gradients. Shimming coils 43 are disposed adjacent gap 49 for providing an additional magnetic field which enhances the uniformity of the magnetic field in the gap. One or more RF transmitting and receiving antennas 91 is also provided adjacent gap 49. The components described above are linked to a conventional MRI imaging system 93 including elements such as DC power supply for energizing coils 48 and 50 and shimming coils 43; RF transmitters and receivers linked to antennas 91; and gradient coil power devices linked to gradient coils 45. The apparatus also is provided with a conventional control computer and conventional components for transforming the received magnetic resonance signals into the desired images. Such elements are well-known in the MRI art and need not be described further herein.

The apparatus further includes raised floor 60 supported above the lower pole support 22 by braces 62. Floor 60 extends over the top of the lower coil 50. A ceiling 64 is suspended beneath upper pole support 20 by ceiling structure members 66. Wall coverings 68 may be provided on the inwardly facing surfaces of connecting elements or walls 24 and 26. Floor 60, ceiling 64 and wall coverings 68 preferably are formed from non-magnetic materials such as polymeric materials, wood fibers, paper and cementitious materials such as concrete, plaster, plasterboard and the like. The exposed, inwardly facing surfaces of the floor, walls and ceiling desirably are formed from standard architectural materials and have the appearance of ordinary room walls. Ceiling 64, wall covering 68 and floor 60 may have standard architectural features such as lamps 65 (FIG. 3) built in. As shown in FIG. 1, floor 60 may be continuous with the floor 70 of a building in which the apparatus is located. Wall covering 68 may be continuous with the walls 72 of the building. Likewise, ceiling 64 may be continuous with a ceiling (not shown) which is part of the building. Thus, the space within the magnet enclosed by floor 60, ceiling 64 and wall covering 68 constitutes part of an ordinary room. The magnet frame, including the pole supports 20 and 22 and the connecting elements 24 and 26 are disposed outside of the room. Also, the coils 48 and 50 are disposed outside of the room. In variants where the interior wall coverings 68, ceiling 64 and floor 60 are not provided, elements of the ferromagnetic frame themselves may define the interior wall surfaces of the room. For example, where wall covering 68 is omitted, the inwardly-facing surfaces of connecting elements 24 and 26 define the interior wall surfaces of the room. In this case as well, the remainder of the connecting element lies outside of the room.

Figure 3:
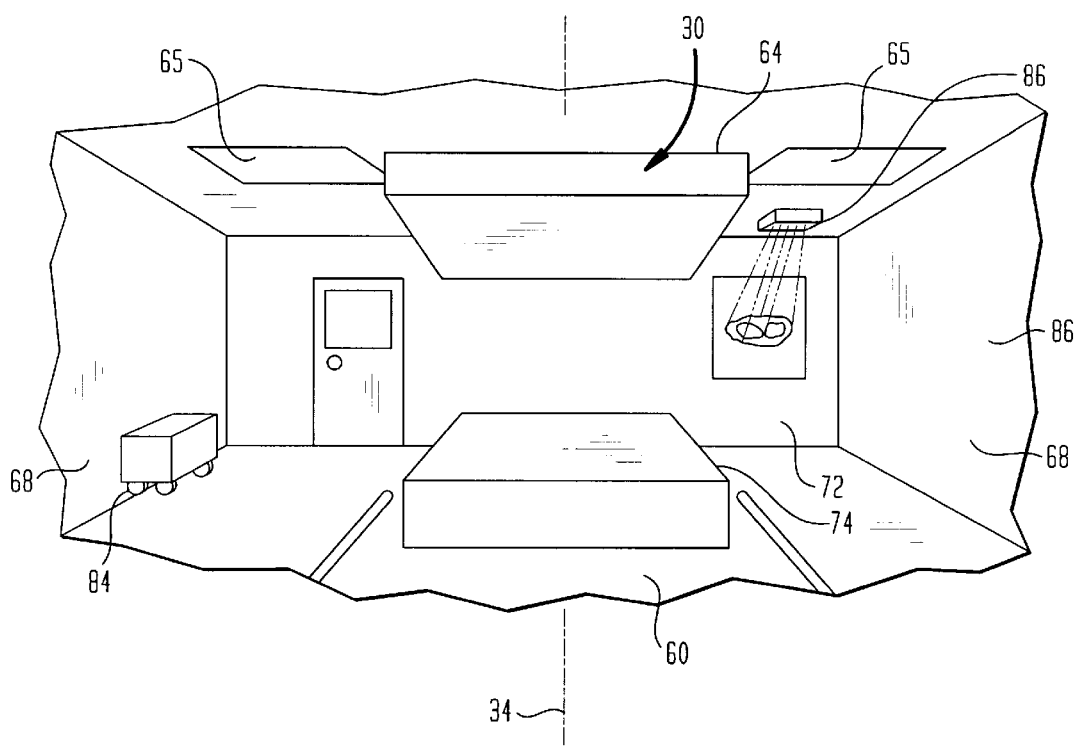
FIG. 3 is a diagrammatic perspective view taken from within the interior of the apparatus shown in FIGS. 1 and 2.

As best appreciated with reference to FIG. 3, a patient or other person inside of the room sees poles 30 and 32 protruding into the room from the ceiling and floor, but otherwise considers the room to be an ordinary room. The poles 30 and 32 desirably are concealed by shrouds 74 (FIG. 3) formed from non-magnetic materials such as polymeric materials. Thus, the apparatus is perceived by a patient as entirely open and non-claustrophobic.

As shown in FIGS. 1 and 2, the connecting elements 24 and 26 are disposed seven feet from polar axis 34. Unless otherwise specified, the distance between the polar axis and the connecting elements specified herein should be understood as referring to the smallest distance from the polar axis to any connecting element in a direction perpendicular to the polar axis, measured at the medial plane of the apparatus such as the radial distance R shown in FIGS. 1 and 2. Because the connecting elements are disposed at substantial distances from the polar axis, an adult human patient P can be positioned on a support, such as a litter or bed 80 (FIG. 2) in a generally horizontal position with his or her body extending close to the medial plane 57 and generally parallel thereto, and the patient can be disposed in any radial direction with any part of his or her body at the polar axis 34. Thus, essentially any part of a normal human patient can be imaged.

A patient positioning device 600 (FIGS. 2, 4 and 5) may be utilized with the magnetic resonance imaging system and magnet to position the patient relative to the poles and magnet gap. Device 600 desirably is formed from non-magnetic materials such as polymers. The positioning device includes a chassis 602 mounted on wheels 604. A pair of rails 606 (FIGS. 1 and 5) extend along the floor 60 of the room and also extend outwardly from the room onto the adjacent floor 70 of the building. Wheels 604 run along these rails so that chassis 602 can be moved along a first horizontal axis, denoted by arrow Z, transverse to the polar axis 34 of the magnet. This first horizontal movement direction is transverse to the long dimension of the poles. As best seen in FIG. 2, chassis 602 includes a pair of vertically-extensive end portions 603 which lie on opposite sides of the lower pole 32 when the chassis is aligned with the polar axis 34 of the magnet. A bridge position 605 of the chassis extends between the end portions, and overlies pole 32 when the chassis is aligned with the polar axis. Breaks (not shown) on wheels 604, or other devices for holding chassis 602 in position on the rails may be provided. In addition, the rails or the adjacent portions of the floor may be provided with graduations, and chassis 602 may be provided with a point or other index mark so that the chassis can be brought to a preselected disposition in the first movement or Z direction. Other positioning devices, such as a screw jack, fixed or adjustable stop or optical positioning system may be employed to locate and index the position of the chassis relative to the floor and the magnet frame.

Figure 4:
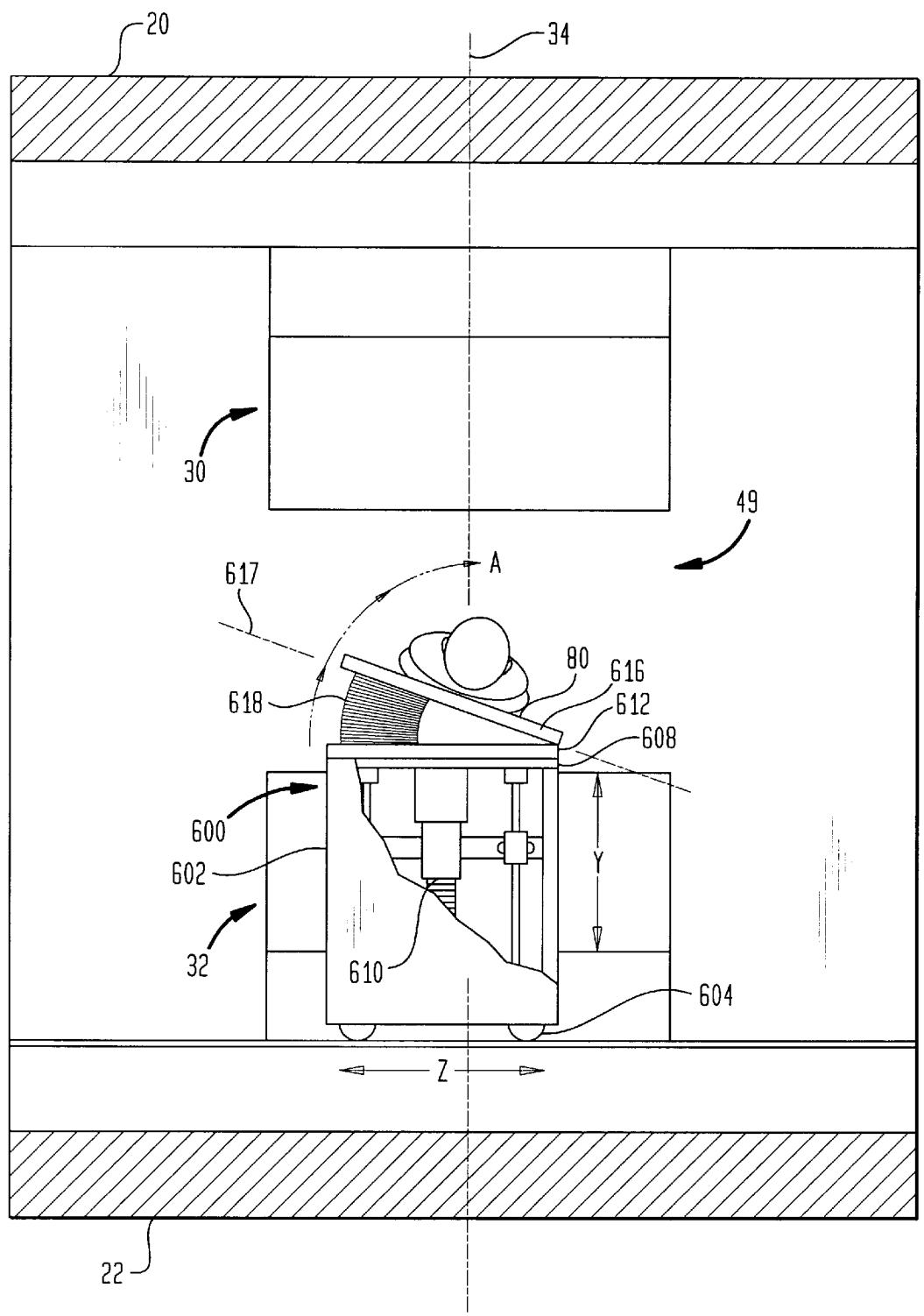
FIG. 4 is a diagrammatic sectional elevational view taken along line 4—4 in FIG. 1.
Figure 5A:
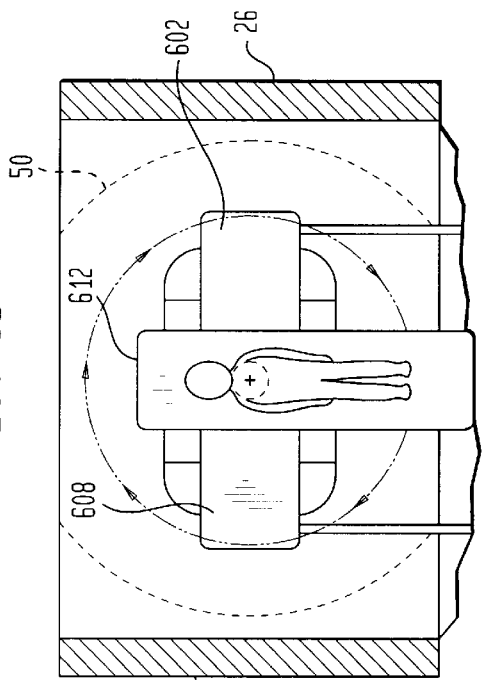
FIGS. 5A to 5D are diagrammatic sectional elevational views taken along line 5—5 in FIG. 1 each such Figure showing arbitrary positions of a patient relative to the polar axis and relative to the remainder of the magnet.
Figure 5B:
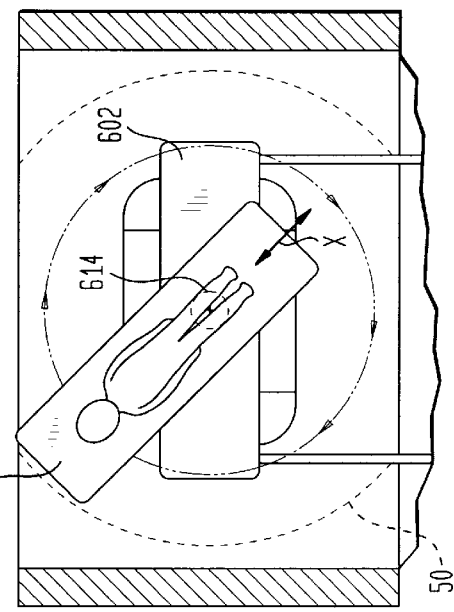
Figure 5C:
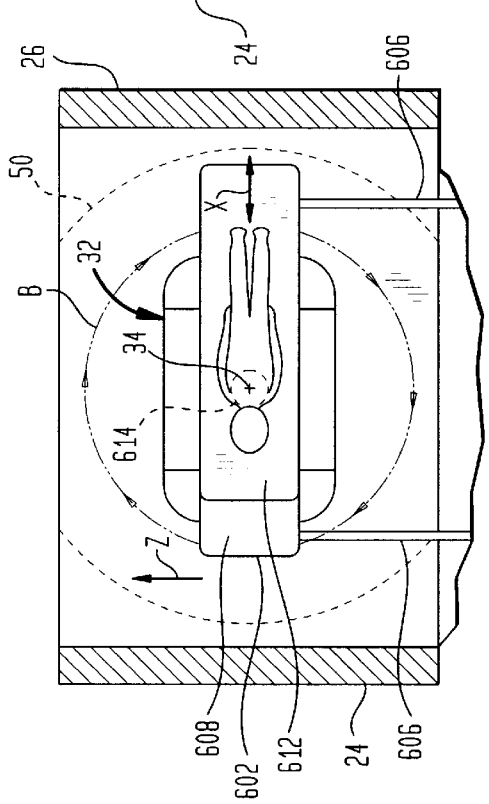
Figure 5D:
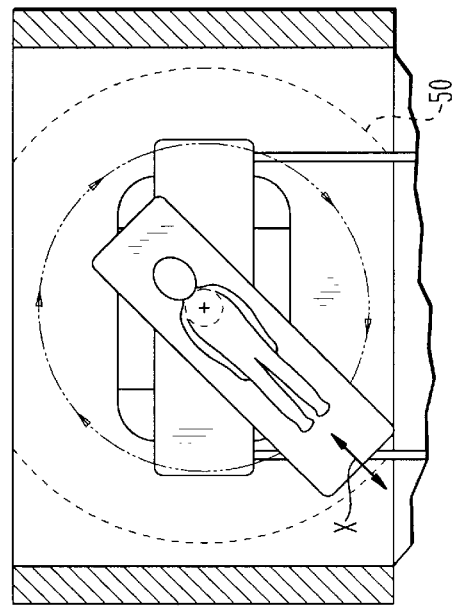

An upper member 608 is mounted on chassis 602. A screw jack 610 (FIG. 4) or other mechanical positioning system such as a hydraulic or pneumatic cylinder, lever system or the like is also provided for moving upper member 608 vertically, in the axial or Y direction, parallel to the polar axis 34 of the magnet. Positioning device 610 may be arranged to displace upper member 608 relative to the remainder of the chassis. Alternatively, upper member 608 may be fixed to the remainder of the chassis and positioning device 610 may be adapted to move the chassis 602 relative to wheels 604. An elongated, movable support 612 is mounted for pivoting movement relative to the chassis and upper member 608 around a pivot 614 (FIG. 5A). Pivot 614 is close to the center of the chassis. Thus, when the chassis is positioned in the Z direction so that the center of the chassis is coincident with the polar axis 34, the pivot 614 is also close to the polar axis. Movable support 612 is also mounted for sliding motion relative to upper member 608 and chassis 602 in a longitudinal direction X, parallel to the long direction of the support itself. Thus, as seen in FIGS. 5A through 5D, the movable support 612 can swing in pivoting motion around pivot 614 so as to orient the longitudinal direction X at any desired angle to the first movement direction Z. Thus, the longitudinal direction X of the movable support can be oriented in any direction relative to the long axis of the rectangular poles 30 and 32. By moving the movable support relative to the chassis 602 in its longitudinal direction, various locations along the length of the a movable support 612 can be aligned with the polar axis 34 of the magnet.

Additionally, the litter or actual patient-carrying device 80 is mounted to the movable support 612 for pivoting movement around a tilt axis 616 parallel to the longitudinal or X direction of the movable support. Thus, as seen in FIG. 4, the tilt axis 616 extends into and out of the plane of the drawing. A tilt actuation device 618, such as a pneumatic bladder or pneumatic cylinder, screw jack, or wedge jack, is provided for tilting the litter through a range of tilt angles A. The patient support is also pivotable relative to the movable support about an inclination axis 617 transverse to the lengthwise direction of the support and transverse to the tilt axis. An inclination actuator (not shown) similar to the tilt actuator is provided for pivoting the support about the inclination axis. This allows positioning of the patient in a Trendlenburg or counter-Trendlenburg position. Thus, the patient positioner 600 provides litter or support 80 with movement in six degrees of freedom: translation in a first lateral direction Z transverse to the polar axis; translation in the X or longitudinal direction of the movable support 612, also transverse to polar axis 34 and at an arbitrary angle to the first or Z direction; rotation in a horizontal plane transverse to the polar axis so as to orient the longitudinal direction X at any angle B relative to the long axes of the poles; elevation or axial movement Y (FIG. 4) parallel to the polar axis; tilt to any desired angle A to the horizontal plane; and inclination so as to raise either end of the support. This provides extraordinary versatility in positioning of the patient relative to the magnet. For example, as seen in solid lines in FIG. 2, the head and neck of the patient is substantially aligned with the polar axis. Translation in the longitudinal direction allows positioning of the feet adjacent the polar axis, as seen in broken lines in FIG. 2. Other, arbitrary positions of the patient relative to the polar axis and relative to the remainder of the magnet are also shown in FIGS. 5A through 5D. Of course, the large clearance within the magnet provided by the ferromagnetic frame discussed above also contributes to the positioning versatility. Because the connecting elements are spaced at a radial distance R from the polar axis of about seven feet or more, longitudinal movement of the patient relative to the frame can be accommodated over a range sufficient to position essentially any part of the patient's body at the polar axis.

The ability to position the patient in essentially any arbitrary location and position relative to the magnet, and relative to the vertical is extremely desirable both in imaging and in image-guided surgery. Certain surgical procedures are best performed in certain orientations of the patient. Also, the best images of the patient are acquired in the region immediately adjacent the polar axis. Therefore, the region of interest of the patient may be positioned at the polar axis to assure optimum imaging of the region of interest.

The system may include more than one patient support 600. In this case, a new patient can be positioned on the patient support and brought to the desired orientation and position at a remote location (not shown) outside of the magnet, while another patient is positioned in the magnet. After the procedure on the existing patient in the magnet is completed, the existing patient can be wheeled out of the magnet on his or her patient support 600 and the new patient support 600, with the new patient thereon, can be rolled into the magnet and positioned in the Z or first movement direction. If the Z or first direction positioning will not vary between successive patients, a fixed stop or lock may be provided, so that the new patient can be fully positioned simply by rolling the new patient support 600 along the rails until the stop or lock is encountered. The ability to position the patient without occupying the MRI system minimizes the idle time of the MRI system between patients and enhances the productivity of the MRI system.

As illustrated in FIG. 2, the physician P is performing an MRI-guided medical procedure on the patient. In this instance, the physician is advancing a surgical probe 650 having an MRI-visible tip into the body of the patient. The imaging system and MRI magnet are operating so as to continually prepare new images of the patient. These images include an image 652 of the surgical probe 650, also showing the patient's internal structures. Thus, as the probe and the internal structures of the patient move, the displayed image including the representation 652 of the probe continues to portray the correct relative positions of the probe and internal structures. The physician therefore can use this image-for guidance as he or she moves the probe and conducts the procedure. Of course, as MRI can also show different tissues within the body in contrast, the physician can use the image of the body structures for guidance in performing the treatment. For example, where a surgical operation is performed to treat a tumor, the MRI system can be operated to acquire an image which shows the tumor in contrast to surrounding normal tissue. The image contrast can be used to monitor the success of the therapy. These capabilities are particularly valuable in performing "minimally invasive" procedures, i.e., procedures which only a relatively small probe such as an endoscope or catheter is advanced into the body, percutaneously or through a small surgical opening or a natural body orifice. Of course, other medical and surgical procedures can be performed while the patient is disposed in the magnetic gap 49 and while MRI imaging is conducted. The environment within the magnet frame constitutes an operating room, and desirably includes the features normally found in operating rooms as, for example, proper lighting sanitation features, life support systems and other surgical apparatus. The essentially unimpeded access to the patient, and freedom of patient positioning provided by the magnet and patient positioning system greatly facilitate performance of these and other medical procedures while the patient is continually imaged by the MRI system. Of course, because MRI does not use ionizing radiation such as x-rays, properly conducted MRI procedures pose no appreciable health risk to the patient or to the physician. The magnetic fields impinging on the physician standing in the work space are minimal. The projecting ferromagnetic poles 30 and 32 concentrate the flux flowing from pole to pole in gap 49, between the poles. The ferromagnetic flux return path, including the pole supports 20 and 22, and the connecting elements 24 and 26 carries the vast majority of the returning flux. Moreover, the large space between the poles and the connecting elements tends to minimize flux leakage from the poles to the connecting elements. Therefore, where the physician is located is the field is minimized. To the extent that any risk is associated with exposure to such magnetic fields, the risk is diminished. Moreover, because only a very small portion of the magnetic flux passes outside of gap 49 between the poles, movement of non-ferromagnetic metallic objects outside of the gap will not induce substantial eddy currents in such equipment. There is minimal magnetic interference with medical equipment disposed in the working space.

The space around poles 30 and 32 provides an unobstructed working space W sufficient to accommodate a physician or other adult human A (FIG. 2). This space is unobstructed by any portion of the magnet frame and extends entirely around the poles and polar axis. Thus, apart from any obstructions which may be created by the patient support 80 or the patient himself, the attendants can have access to the patient from all locations. This working space W extends to the region of the magnet between coils 48 and 50. Thus, a portion of the working space is disposed above the lower coil 50 and below the upper coil 48. The degree of access afforded by the apparatus is essentially the same as the degree of access provided in an ordinary operating room, with only a slight obstruction caused by poles 30 and 32 themselves. That obstruction is minimized by the relatively small diameter of the poles and the relatively large space between the poles.

Equipment for performing medical procedures on a patient, such as an anesthesia ventilator 84 (FIG. 2), or any other type of conventional medical equipment may be disposed inside the room, within the interior of the magnet frame. Further, a display device such as a projection unit 86 (FIG. 2) connected to the computer associated with the MRI system desirably is mounted to display an image inside the room, so that a physician or other persons performing medical procedures on a patient within the apparatus can observe the MRI image in real time, while performing such procedures. For example, one suitable projection unit is an LCD projector made by Boxlight Corporation of Paulsboro, WA. The projection unit is a particularly desirable display because it provides a large image which can be seen-by all members of the medical team in the room. One or more conventional CRT monitors and/or video goggles as discussed below can also be utilized. Control apparatus 87 such as a keyboard, joystick, mouse, or touch-sensitive elements on a monitor may also be provided inside the room, so that the attendant can control the MRI imaging process from within the room. Preferably, the working space W and gap 49 are shielded from radio frequency interference, to prevent interference with the MRI imaging procedure. Thus, the room preferably is surrounded with a continuous or substantially continuous electrically conducted shield, commonly referred to as a Faraday shield. Because the pole supports 20 and 22 and connecting elements 24 and 26 of the magnet frame are electrically conductive, these elements may serve a portion of the Faraday shield. In addition, the floor 70 and wall 72 of the building, as well as the ceiling of the room may be provided with conductive elements such as conductive mesh 88 (FIG. 1). The conductive mesh may be electrically connected to the magnet frame as by a wire or bonding strap (not shown) connecting the mesh to the frame. Doors 90 and windows 92 penetrating these walls are also provided with conductive coverings such as mesh in the doors and conductive films on windows. These conductive coverings desirably are also connected to the remainder of the faraday shield. The equipment disposed inside of the room, and hence inside of the faraday shield is designed for low RF emission. For example, the video monitor 86 may be provided with an enclosure having a conductive shield which is grounded to the frame. Also, fixtures such as overhead lights 65 may be provided with a similar shielding.

The pole supports 20 and 22, connecting elements 24 and 26, and poles 30 and 32 are arranged to provide a path with low magnetic reluctance for the flux generated by coils 48 and 50. The flux is relatively concentrated in the poles and in regions of the upper and lower pole supports adjacent the polar axis 34. Thus, the magnetic field achievable with the magnet may be limited by magnetic saturation of the ferromagnetic material in these regions. Magnets according to the present invention typically provide fields of at least about 0.5 kilogauss, preferably at least about 1 kilogauss, more preferably at least about 3 kilogauss and desirably at least about 6 kilogauss in gap 49, but may include magnets operating at considerably higher field strengths. For example, to provide a field of about 6 kilogauss, each of coils 48 and 50 may include about 220 turns, and may be energized at a current of about 1,000 amperes to provide about 220,000 ampere-turns each. Ferromagnetic material of relatively high permeability, preferably equal to or greater than the permeability of grade 1006 steel is used in the central regions of the pole supports and in the pole stems. Preferably, the high permeability magnetic material has a permeability of at least about 50 at a field strength of 20 kilogauss or higher within the ferromagnetic material. Very high permeability materials, such as grade 1001 steel, having a permeability in excess of 50, at a field of 22 kilogauss is even more preferred.

In the regions of the pole supports remote from the polar axis and in the connecting elements, the magnetic flux spreads out over the entire the width and thickness of the ferromagnetic material. Therefore, the magnetic flux is substantially less concentrated in these regions and magnetic material of lower permeability can be used if desired. Moreover, because the pole supports and connecting elements are disposed outside of the space occupied by the patient and the attendant, the size of these elements is essentially unlimited. Adding more material does not impede access to the patient. Thus, essentially any ferromagnetic material of modest magnetic conductivity can be provided in these elements without impairing access to the patient, simply by providing more ferromagnetic material. Accordingly, in these regions of the frame, the choice between using a relatively thin element at high permeability material and a thick element of lower permeability material is controlled by considerations such as economics and the weight of the resulting structure.

Coils 48 and 50 may be replaced by superconducting coils. Superconducting coils typically are enclosed in vessels referred to as cryostats filled with a coolant such as liquid helium for conventional low temperature superconductors such as NbTi or $Nb_3Sn$ or, preferably, liquid nitrogen for high temperature superconductors. The coolant maintains coils at temperatures low enough to provide superconductivity. The required temperature of course depends upon the composition of the superconducting material. Preferred promising superconducting materials such as BSCCO and YBCO provide superconductivity at temperatures of about 77° K. the boiling point of liquid nitrogen, or at even higher temperatures (see for example Superconductive Components, Columbus, OH, Eurus Technologies, Inc., Tallahassee, Fla.). This minimizes the amount of energy which must be expended to cool the coils and also greatly simplifies the design of the cryostats and associated components. The superconducting coils in their cryostats include the poles in the same positions as conductive coils 48 and 50, for example, located above the ceiling and below the floor. Thus, the working space W desirably extends above one cryostat and below the opposite cryostat. However, for very high current densities small cross-section coils may alternatively be located surrounding the poles in place of the blocking magnets discussed below with reference to FIG. 8. As described, for example, in U.S. Pat. No. 4,766,378, use of a ferromagnetic frame with projecting ferromagnetic poles in conjunction with superconductive coils is particularly advantageous. The ferromagnetic frame tends to stabilize the superconducting coil and reduce field nonuniformities caused by coil movement. The present invention thus affords a way to attain the benefits disclosed in the '378 patent while also providing essentially unlimited access to the patient. Superconducting coils can be used for low fields but are particularly useful where a very high magnetic field, above about 6 kilogauss is desired within the gap.

As shown in FIG. 6, apparatus according to a further embodiment of the invention utilizes a frame 100 having permanent magnets as the source of magnetic flux. For example, the connecting elements 124 and 126 include magnetic blocks formed from a "hard" magnetic material, i.e., a magnetic material having high coercivity which is resistant to demagnetization. Alternatively or additionally, permanent magnets may be provided in the upper pole support 120, in the lower pole support 122, or in poles 130 and 132 themselves. Here again, because the pole supports 120 and 122 and the connecting elements 124 and 126 are disposed outside of the working space W, and outside of the space occupied by the patient, there is essentially no physical limit on the size of these elements. Therefore, these elements may incorporate essentially any amount of permanent magnet material. This facilitates the use of relatively low-energy magnet materials as an alternative to high energy product materials to provide some or all of the magnetic flux.

Figure 7:
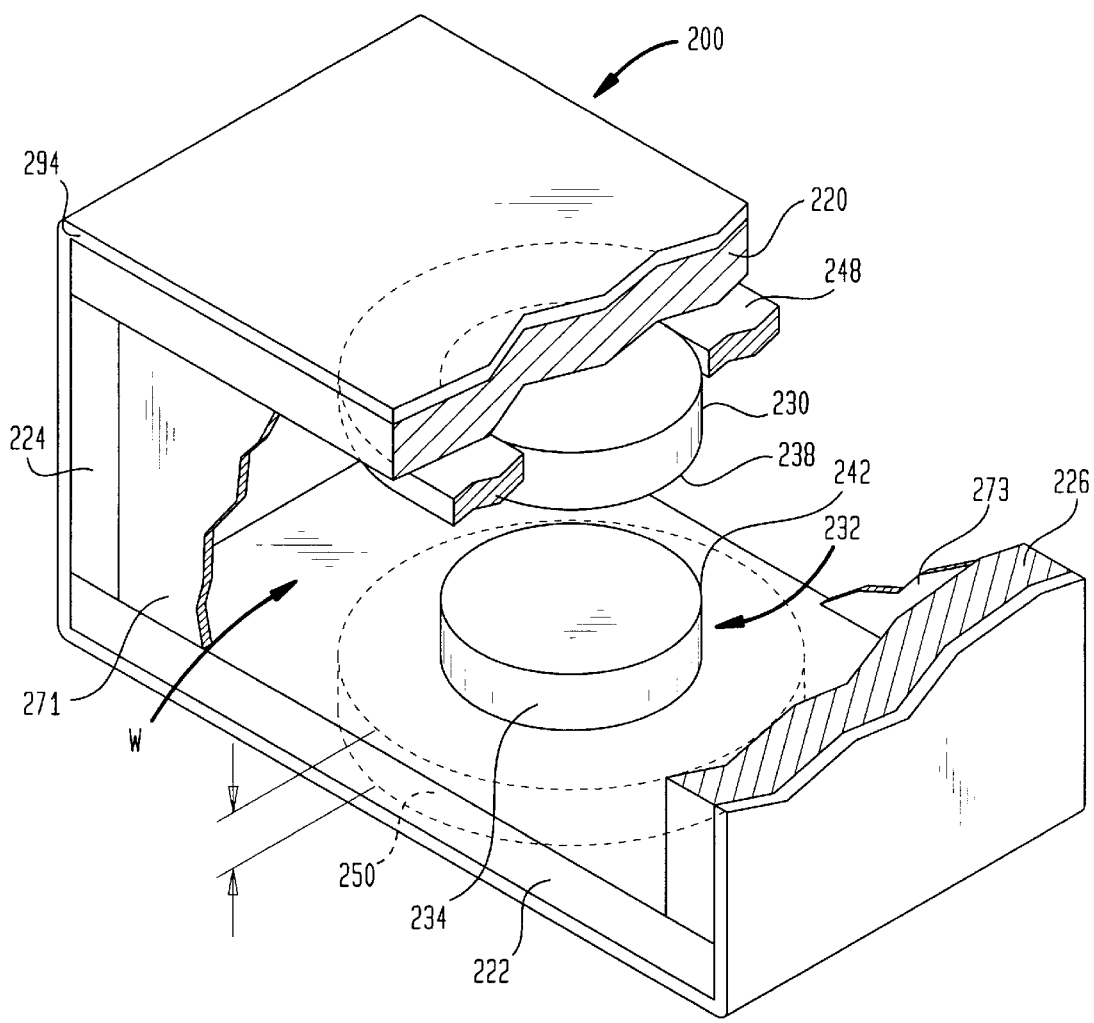
FIG. 7 is a diagrammatic perspective view depicting apparatus according to a further embodiment of the invention.

As shown in FIG. 7, apparatus in accordance with a further embodiment of the invention includes a frame 200 having pole supports 220 and 222 and connecting elements 224 and 226 similar to those discussed above. The frame includes upper and lower poles 230 and 232, which are generally cylindrical, and about 48 inches in diameter. The distance between pole tips 238 and 244 and hence the dimension of gap 249 in the axial direction along polar axis 234 desirably is about 36 inches. Here the ratio of the shortest dimension of the pole tips transverse to the polar axis 234 (the diameters of the pole tip) to the axial dimension of the gap distance is about 1.75:1. As discussed above with reference to FIG. 1, this ratio desirably is between about 1:1 and about 2:1.

Figure 8:
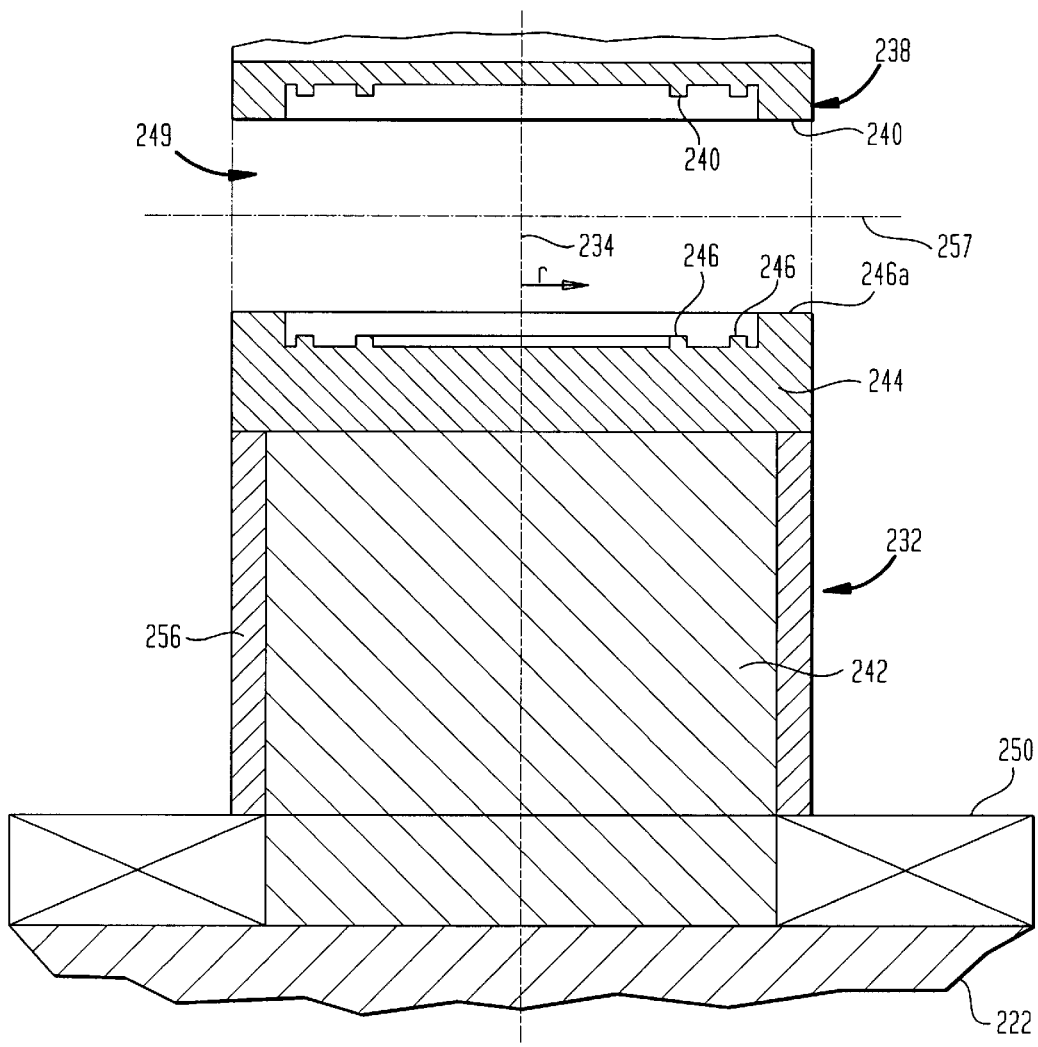
FIG. 8 is a fragmentary sectional view depicting a portion of the apparatus shown in FIG. 7.

As depicted in FIG. 8, lower pole includes a ferromagnetic stem 242 extending from the lower pole support 222 and a ferromagnetic tip element 244 at the distal end of the pole stem, remote from the pole support. Tip element 244 is provided with annular ridges 246 at various radial distances r from the polar axis 234. In the arrangement shown, one such ridge 246a is disposed at the outer edge of the pole tip. The upper pole tip 238 is provided with matching annular ridges 240. The ridges 246 and 240 effectively reduce the axial distance across gap 249. Thus, the ridges shape of the pole surface to alter the reluctance at preferred geometric locations. The pattern of these different reluctances is selected to enhance the uniformity of the field in gap 249. This allows use of a smaller ratio of pole diameter to gap size than would otherwise be required to achieve the same field uniformity. Other structural elements which provide differing reluctances at different locations relative to the polar axis can be employed. For example, the pole stems or pole tips may have internal gaps filled with non-ferromagnetic material to provide increased reluctance at some locations.

Optionally, pole 232 may include a set of bucking elements 256 encircling pole stem 242 between coil 250 and pole tip element 244. The upper pole 230 may include a similar set of bucking elements (not shown). Coils 248 and 250 are energized to direct flux in a forward direction along the poles, so that the flux process in the forward direction through gap 249. Bucking elements 254 and 256 include permanent magnets arranged to direct flux in a rearward direction, opposite to the forward flux direction. For example, coils 248 and 250 may be activated to direct flux downwardly out of upper pole 230 and into lower pole 232, through gap 249, so that the forward direction is the downward direction. The bucking elements are arranged to direct flux into pole 230 and out of pole 232, in the rearward or upward direction. This arrangement tends to confine the flux from the coils within the poles and tends to minimize leakage of flux from the peripheral surfaces of the poles. This tends to promote a substantially unidirectional, uniform magnetic field within the region of the gap 249 adjacent the polar axis 234 and adjacent the medial plane 257, midway between the pole distal ends.

Here again, the working space W immediately surrounds the poles, so that a physician or other attendant can be positioned inside the working space to have access to a patient while the patient is disposed in the gap between the poles. Here again, the working space W extends above one coil and beneath the opposing coil.

The ferromagnetic frame also may include ferromagnetic walls 271 and 273 extending between the pole supports on the long edges of the pole supports, i.e., on the edges of the pole supports which are not occupied by the connecting elements 224 and 226. Thus, the pole supports form two opposing sides of a hollow rectangular solid; the connecting elements 224 and 226 form two other opposing sides or wall elements and walls 271 and 273 form the remaining opposing sides or wall elements. Walls 271 and 273 desirably have openings (not shown) formed therein to provide access by a patient and an attendant to the interior of the frame. Walls 271 and 273 may be relatively thin metallic structures. These additional walls minimize leakage flux from the exterior of the frame. Conversely, these additional walls block the effects of varying magnetic fields outside of the frame on the field between the poles, and thus provide a more uniform, stable field. Also, walls 271 and 273 form electrically conductive elements of a Faraday shield to minimize RF interference with the MRI imaging procedure.

In a variant of the apparatus discussed above, the frame may be provided with a layer or shell of bucking flux elements 294 overlying the ferromagnetic elements of the frame on the outside of the frame. The bucking flux elements are permanent magnets arranged to direct flux along the exterior of the frame in a direction opposite to the direction of the flux induced by coils 248 and 250.

Figure 9:
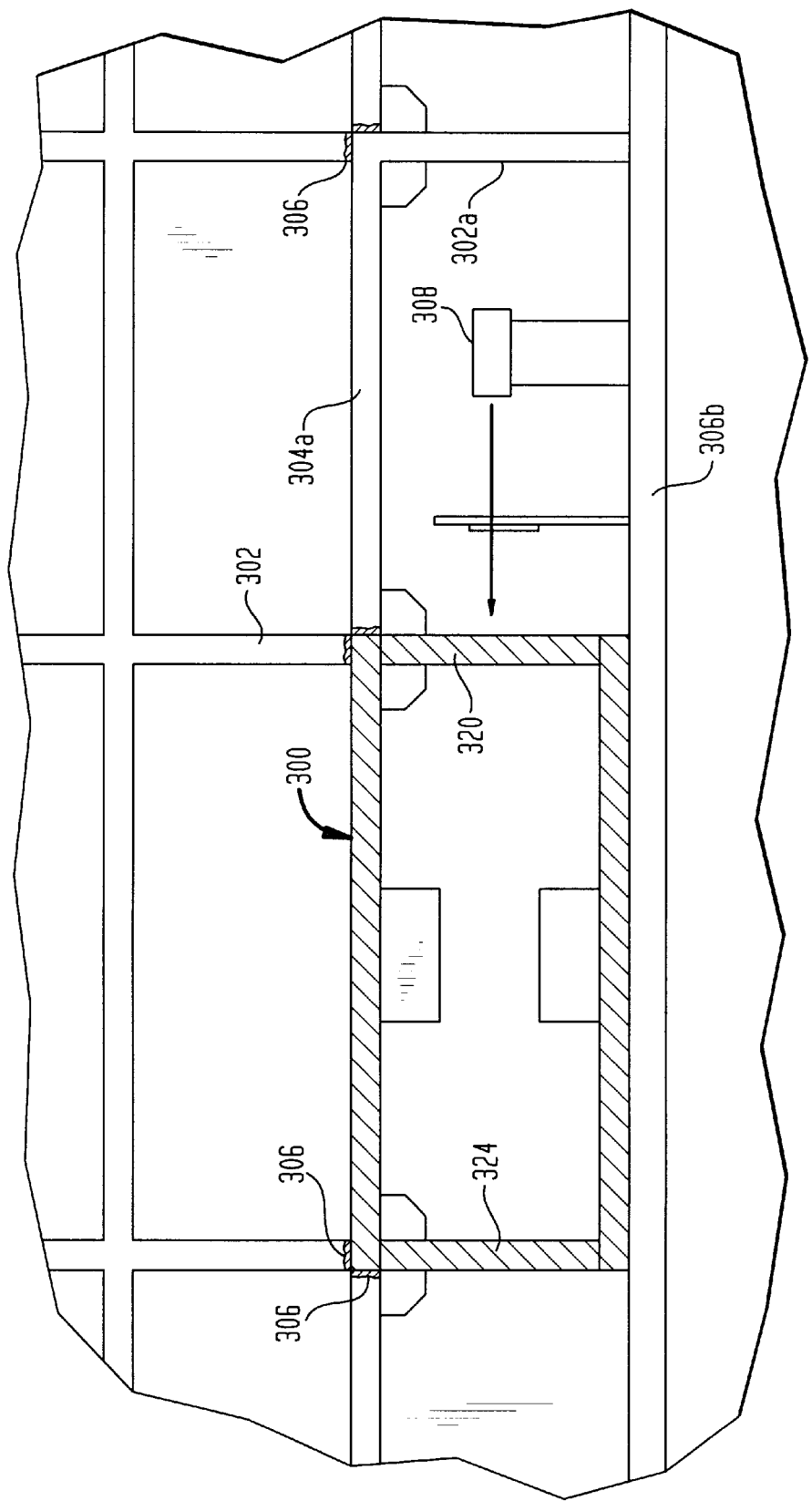
FIG. 9 is a diagrammatic elevational view depicting apparatus in accordance with a further embodiment of the invention in conjunction with a building and other apparatus.

As shown in FIG. 9, the magnet frame may be integrated with the structure of a building. For example, the connecting elements 324 and 326 of a magnet frame as discussed above may support other structural elements, such as columns 302 and beams 304. Where the beams and columns are ferromagnetic, such as in conventional steel frame construction, blocking plates 306 framed from a diamagnetic material may be interposed between the frame of the MRI magnet and the remainder of the building frame to prevent transmission of magnetic flux herebetween. This minimizes any effect of induced magnetic fields in the remainder of the building frame on the MRI imaging procedure. Alternatively, other parts of the building frame may be integrated in the magnetic circuit of the magnet frame. Thus, beam 304a, column 302a and beam 304b are connected in magnetic circuit in parallel with connecting element 326 and carry part of the magnetic flux. These elements may be isolated from other parts of the building frame by further blocking elements 306. Those elements of the building frame connected in the magnetic circuit may be protected from induced magnetic fields by appropriate shielding (not shown) or else may be located in areas of the building remote from sources of interfering magnetic field as, for example, areas remote from heavy electrical generating equipment and vehicular traffic. As also shown in FIG. 9, elements of the ferromagnetic frame may provide shielding for ionizing radiation such as x-rays or gamma rays used in therapeutic procedures. Thus, the ferromagnetic frame may be located adjacent a MRI operating room housing an x-ray or gamma ray treatment unit 308, and the treatment unit may be arranged to direct radiation towards the ferromagnetic frame. Connecting element 326 serves as a shielding wall. Alternatively or additionally, radiation-generating equipment may be disposed inside of the ferromagnetic frame, and hence inside of the room surrounded by the frame. Using these approaches, the cost of installing the ferromagnetic frame can be offset in part by cost savings achieved by eliminating other shielding structures which ordinarily would be provided in a hospital setting for the gamma ray or x-ray devices.

Figure 10:
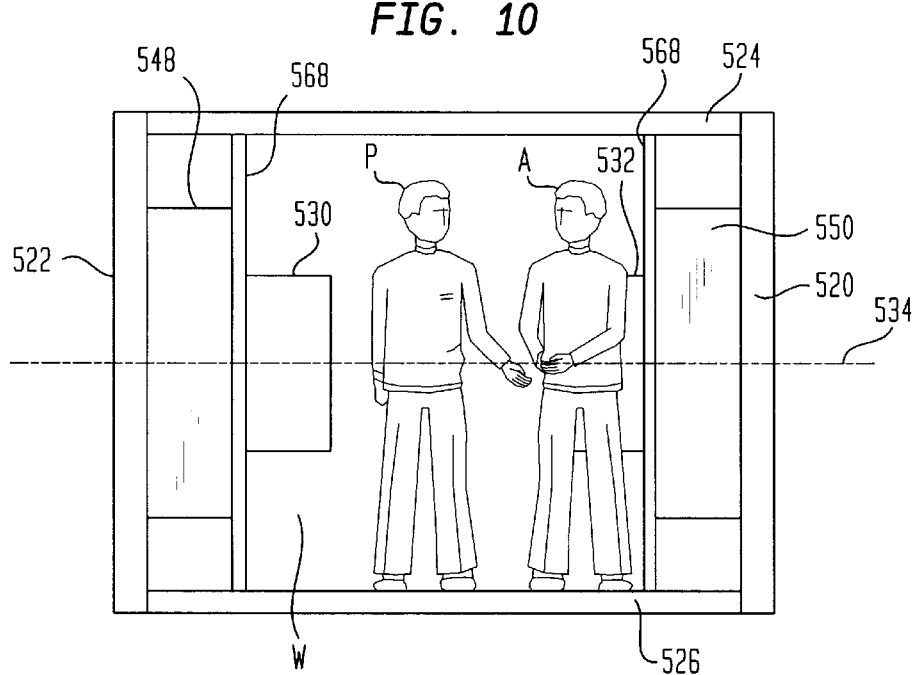
FIG. 10 is a diagrammatic elevational view depicting apparatus in accordance with a further embodiment of the invention.

As shown in FIG. 10, a magnet in accordance with a further embodiment of the invention has a polar axis 534 oriented generally horizontally, and has vertically oriented pole supports 520 and 522. Poles 530 and 532 project horizontally inwardly from the pole supports. The connecting elements 524 and 526 extend substantially horizontally. In the arrangement illustrated, coils 548 and 550 encircle the poles and are disposed in generally vertical planes adjacent the pole supports. Here again, the apparatus defines a working space W sufficient to accommodate a normal human attendant A. Once again, concealment structures such as false walls 568 may be disposed inside of the magnet frame to conceal the magnet frame from a patient. The patient has the visual impression of entering a room where the poles 530 and 532 protrude from opposing walls of the room, rather than from the floor and ceiling. Alternatively, the coils 548 and 550, and walls 568 can be moved closer to the pole tips in this configuration. Apparatus with horizontally-projecting poles can be used, for example, to image a patient P while the patient remains in a generally vertical orientation as, for example, in a standing position or a position close to the standing position. The same apparatus can also be used to form an image of the patient while the patient is in a seated or reclining posture, or in essentially any other position desired. This offers considerable benefits in diagnosing and treating conditions which vary with the patient's posture as, for example, certain orthopedic conditions. Here again, the large space within the magnet frame allows the attendant to have free access to the patient while the patient is being imaged.

Figure 11:
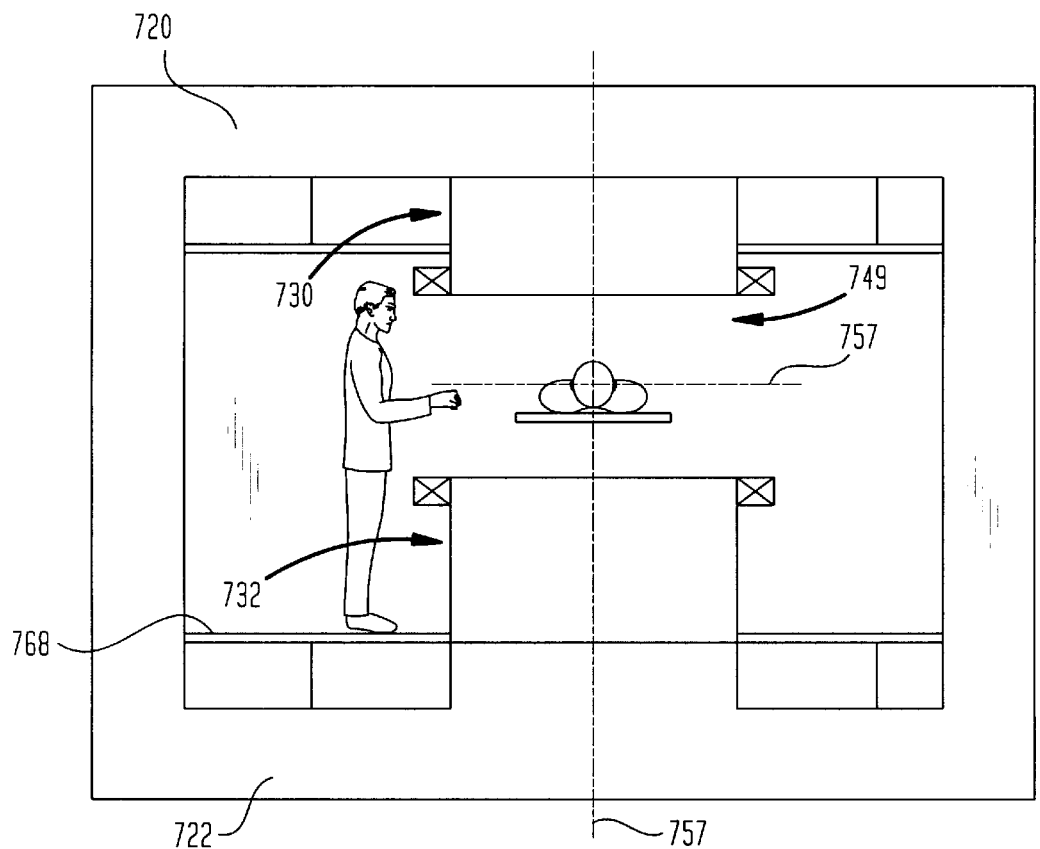
FIG. 11 is a diagrammatic sectional view depicting apparatus in accordance with yet another embodiment of the invention.
Figure 12:
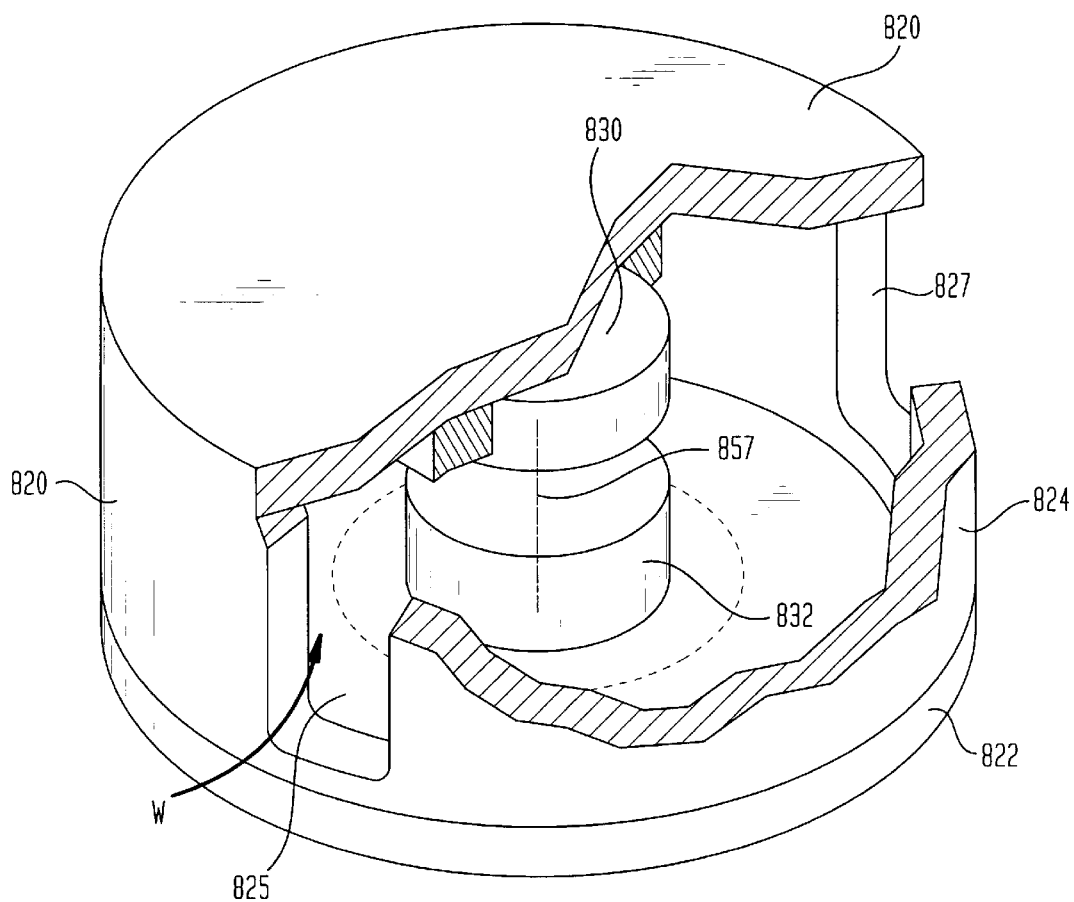
FIG. 12 is a diagrammatic perspective view depicting apparatus in accordance with a further embodiment of the invention.

As shown in FIG. 11, a magnet in accordance with a further embodiment of the invention has poles of different lengths in the axis direction. Thus, the upper pole 730 is shorter than the lower pole 732 in the axial direction, along the polar axis 757. Therefore, the medial plane 757 of the gap 749 is closer to the upper pole support 720 than to the lower pole support 722. The opposite arrangement, wherein the lower pole is shorter and the medial plane is closer to the lower pole support can also be used. Thus, by selection of appropriate pole lengths, the medial plane of the gap can be disposed at any desired elevation to facilitate positioning of the patient at a convenient height for the physician while still maintaining the area of interest of the patient in the region adjacent the medial plane of the gap, where image quality is optimized. In magnets using unequal-length poles, additional flux-shaping devices such as auxiliary coils 755, auxiliary magnets and/or shaped pole tips preferably are provided to maintain flux uniformity. In an extreme case, one of the projecting poles may be eliminated entirely, so that the gap is defined between the tip of a single projecting pole and a polar region on the face of the opposite pole support. Thus, the plate constituting the pole support serves as the pole as well. In such an arrangement, the flux-generating winding may extend around the polar region and on the surface of the pole support plate. The asymmetry of this extreme arrangement typically requires use of features such as compensating shapes on the pole tip and/or on the polar region itself, and auxiliary shim coils. The principal energizing coils of the magnet may also be asymmetric to provide additional compensation.

A magnet in accordance with yet another embodiment of the invention incorporates a generally cylindrical ferromagnetic frame. Thus, the connecting elements 824 and 826 are generally in the form of sectors of a cylinder or other body of revolution coaxial with the polar axis 857. A pair of openings 825 and 827 are provided on opposite sides of the polar axis for ingress and egress of patients and medical personnel. The upper and lower pole supports 820 and 822 are in the form of circular plates. In this particular embodiment, the poles 830 and 832 are cylindrical. However, elongated, non-circular poles, such as the rectangular poles discussed above can be employed in this embodiment as well. The working space W within the frame is in the form of an annulus encircling the poles and concentric with the polar axis.

Figure 13:
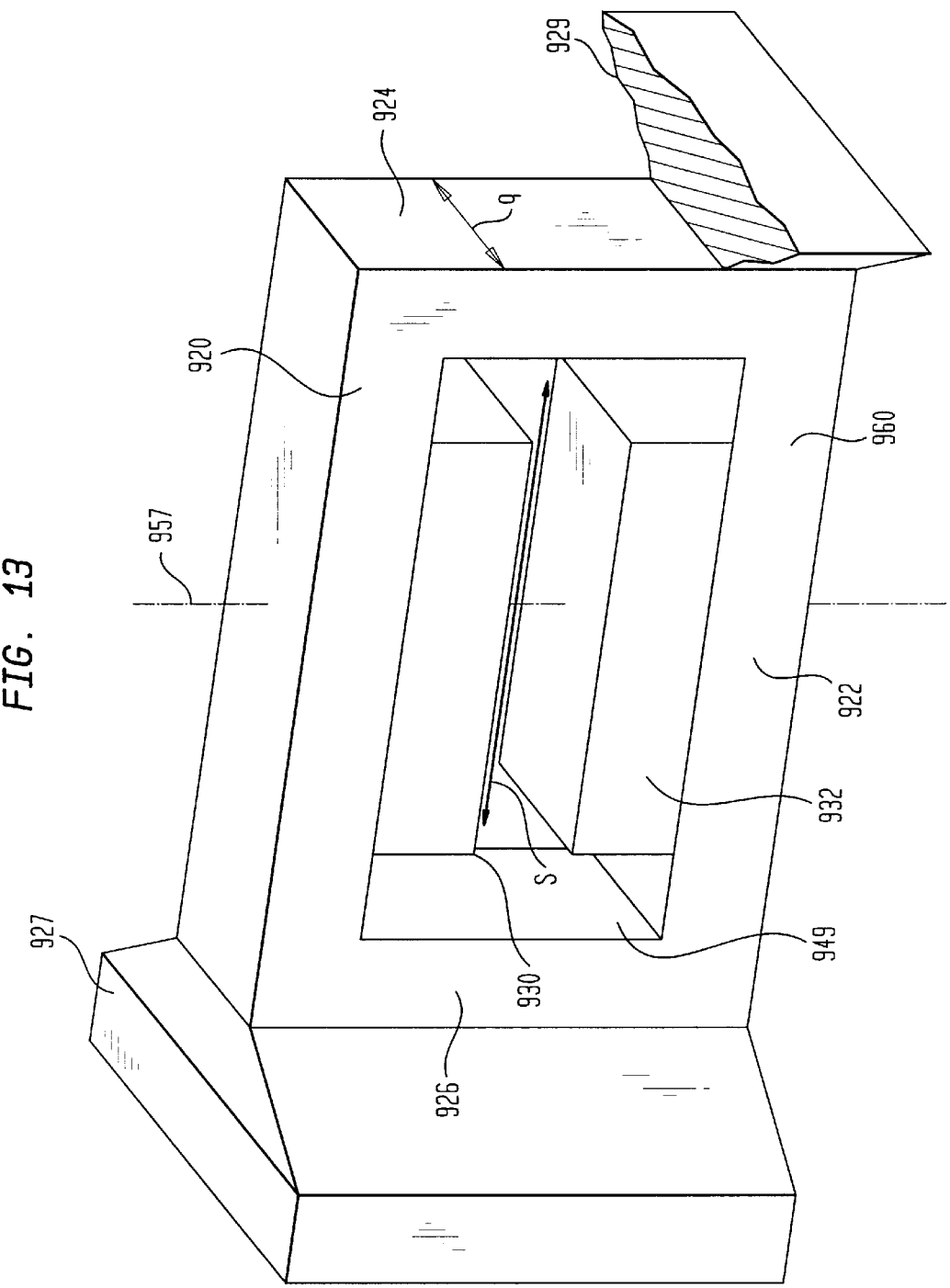
FIG. 13 is a diagrammatic perspective view depicting apparatus in accordance with a still further embodiment of the invention.

A magnet as shown in FIG. 13 has a generally flat frame. That is, the widthwise dimensions q of connecting elements 924 and 926 are not substantially larger than the corresponding widthwise dimensions of poles 930 and 932. Preferably, the widthwise dimensions q of the connecting elements in this embodiment are about 48 inches or less at least in those regions of the connecting elements closest to the gap 949. The regions of connecting elements 924 and 926 remote from gap 949 can be of essentially any dimensions. Thus, as depicted in FIG. 13, connecting element 926 includes an outwardly flowing portion 927 remote from the gap and connecting element 924 includes a similar broad portion 929 also remote from the gap. These broad portions are optional.

Desirably, the distance S between the interior surfaces of connecting elements 924 and 926 along a lengthwise dimension transverse to the polar axis and transverse to the widthwise dimensions is at least about 7 feet and most preferably between about 7 feet and about 14 feet. Poles 930 and 932 are elongated. The long dimensions of the poles extend in the direction, from one connecting plane 924 to the opposite connecting element 926. In this arrangement, the frame may not define a working space inside the frame itself sufficient to accommodate a physician or other person. For example, the edges of pole 932 may lie close to the interior surfaces of the connecting elements 924 and 926 that a person cannot enter between the pole and the connecting elements. However, because those portions of the connecting elements lying close to the gap have a relatively short widthwise dimension q, a person standing outside of the frame, but alongside the frame next to the pole, can still have reasonable access to the patient disposed in gap 949. As in the embodiments discussed above, the elongated poles provide an elongated region of uniform magnetic field for imaging. The flux source is not depicted in FIG. 13. The flux source may be disposed at any location where it does not impede access. For example, the flux source may include permanent magnets incorporated into the frame. Alternatively, coils may extend around the connecting elements or the poles. If the coils extend around the connecting elements, then the distance S between the connecting elements desirably is increased to compensate for the space occupied by the coil, so that the clear span between the interior faces of the coils is at least about 7 feet and desirably between 7 feet and 14 feet.

Figure 14:
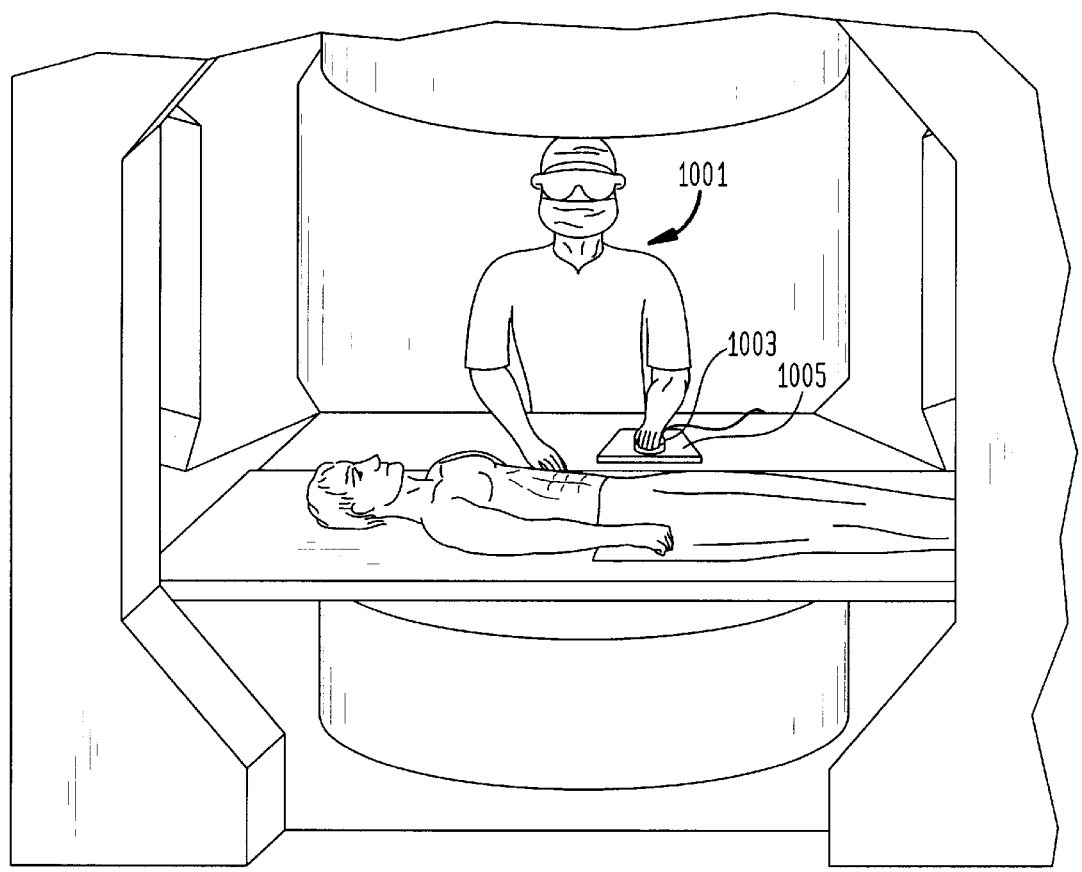
FIG. 14 is a diagrammatic perspective view depicting apparatus in accordance with another embodiment of the invention.

As depicted in FIG. 14, a further embodiment of the invention utilizes video display goggles 1001 connected to the magnetic resonance imaging unit to provide a visible display of the MRI image to the physician. The video display goggles may be arranged to display the image in front of the physician's eyes upon command. At other times, the video display goggles provide a clear vision so that the physician can see the patient in the normal manner. Alternatively, the video display goggles may be arranged to provide the MRI image superposed on the normal field of view so that the physician can observe both the MRI image and the patient simultaneously. Such superposition can be achieved, for example, using the superposition methods commonly employed in "heads up display" technology. Alternatively, the video goggles may be adapted to provide the MRI image in a corner of the visual field, so that the physician can see the image by turning his or her eyes in a particular direction as, for example, by rolling his or her eyes, away from the patient.

As also seen in FIG. 14, a mouse 1003 and a mouse pad 1005 are employed. Thus, the user interface of the MRI imaging system may incorporate a graphical user interface, wherein the user positions a cursor over a box or button appearing in the visual display and then actuates a button on the mouse to instruct the system to perform a particular action. The graphical user interface display may be shown in the same video goggles 1001 as used to display the MRI image. The mouse and graphical user interface may also be employed with a video display, such as with a projection display as discussed above with reference to FIGS. 1–3. The same mouse may be used to control a surgical robot including a surgical probe, needle or catheter. Also, both the option of the mouse control and the display options such as video goggles and projection are usable with other magnet frames, apart from those discussed above.

Figure 15:
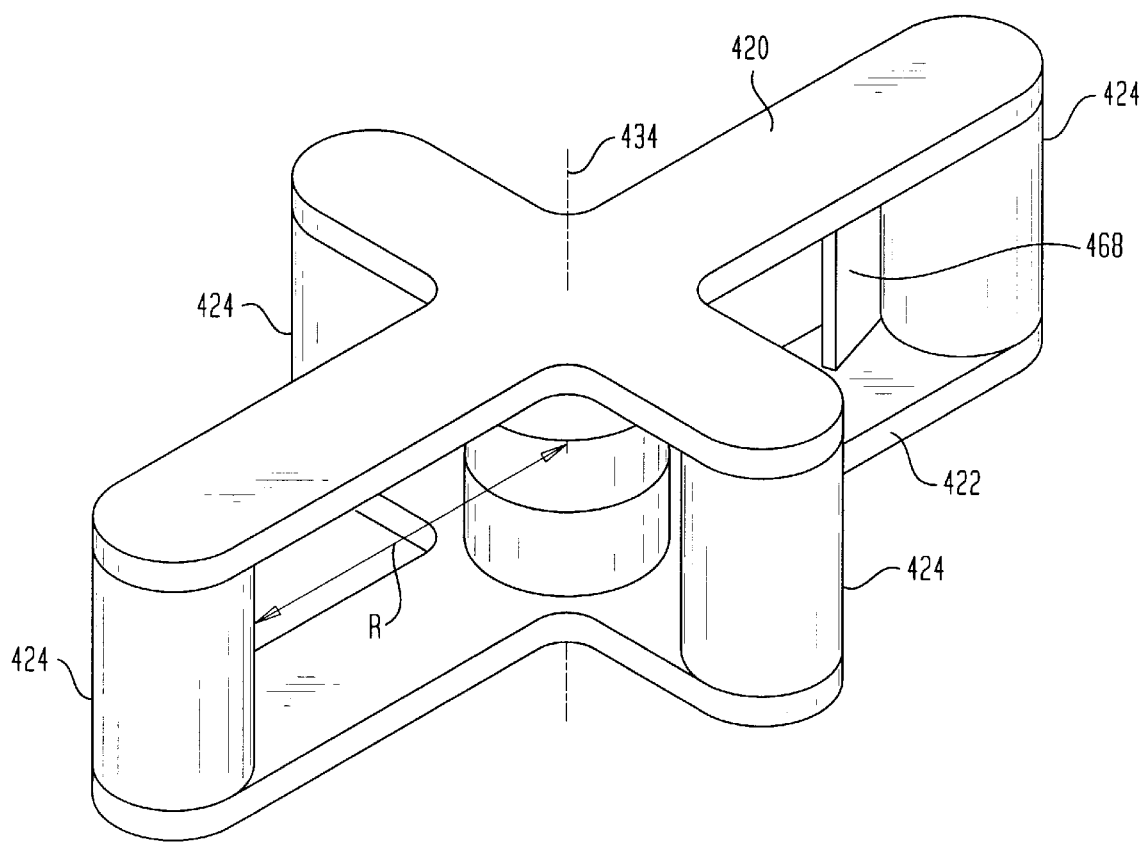
FIG. 15 is a diagrammatic perspective view depicting apparatus in accordance with another embodiment of the invention.

The configuration of the magnet frame can be varied considerably from those discussed above. For example, the pole supports 424 utilized in the frame of FIG. 15 are columns spaced widely apart from one another, rather than rectangular plates. Also, the pole supports 420 and 422 are generally star-shaped or x-shaped, and include individual legs extending away from the polar axis 434 towards each of the pole supports. Here again, the pole supports desirably are spaced at a distance R from the polar axis sufficient to provide a substantial working space around the poles. Here again, concealment elements such as a wall 468, floor (not shown) and ceiling (not shown) may be exposed inside of the region encompassed by the pole supports and connecting elements so as to define a room to conceal the frame from the patient. The overall impression again may be the impression of a normal room as discussed above with reference to FIG. 3.

Numerous variations and combinations of the features discussed above can be utilized without departing from the present invention as defined by the claims. For example, in those embodiments where non-circular poles are employed, the pole may be generally elliptical or other shapes different from the generally rectangular poles discussed above. Accordingly, the foregoing description of the preferred embodiments should be taken by way of illustration rather than by way of limitation of the invention as claimed.

What is claimed is:

1. A magnet for magnetic resonance imaging apparatus comprising:
   (1) A ferromagnetic frame including:
      (a) a pair of opposed ferromagnetic pole supports spaced apart from one another;
      (b) a pair of ferromagnetic poles connected to said pole supports, said poles projecting from said pole supports toward one another along a polar axis, said poles having distal ends spaced apart from said pole supports, said distal ends confronting one another and being spaced apart from one another by a gap distance so as to define a patient-receiving gap therebetween;
      (c) one or more connecting elements extending between said pole supports, said connecting elements being remote from said poles in a direction or direction transverse to said polar axis; and
   (2) a source of magnetic flux adapted to direct flux through said frame so that said flux passes between said distal ends of said poles through said gap and returns through said pole supports and said connecting elements,
   said magnet defining a working space within said ferromagnetic frame alongside of said poles sufficient to accommodate one or more physicians, whereby a physician in said working space can have access to a patient disposed in said gap.

2. A magnet as claimed in claim 1 wherein said working space extends between said pole supports and extends between said poles and said connecting elements.

3. A magnet as claimed in claim 1 wherein each of said poles has a distal end with a long dimension and a short dimension, the long dimensions of said distal ends being aligned with one another.

4. A magnet as claimed in claim 3 wherein the ratio of the long dimension of each said pole distal end to the short dimension thereof is at least about 4/3.

5. A magnet as claimed in claim 4 wherein said long dimension of each said pole distal end is at least about 60 inches.

6. A magnet as claimed in claim 5 wherein said poles define a gap distance therebetween in the direction of said polar axis, and wherein the ratio of the short dimension of each said pole distal end to the gap distance is between about 1:1 and about 2:1.

7. A magnet as claimed in claim 3 wherein said poles are generally rectangular.

8. A magnet as claimed in claim 7 wherein said poles taper so that the long dimension of each pole decreases in the direction towards the distal end of the pole.

9. A magnet as claimed in claim 3 wherein said poles are generally elliptical.

10. A magnet as claimed in claim 3 wherein the ratio of said short dimension to said gap distance is about 2:1 or less.

11. A magnet as claimed in claim 10 wherein the ratio of said short dimension to said gap distance is between about 1:1 and about 2:1.

12. A magnet as claimed in claim 10 wherein said long dimension is at least about 4/3 times said short dimension.

13. A magnet as claimed in claim 1 wherein each said pole has a generally rectangular tip at its distal end.

14. A magnet as claimed in claim 1 wherein each of said poles has a substantially circular tip at its distal end.

15. A magnet as claimed in claim 14 wherein the ratio of the diameter of each said pole tip to said gap distance is between about 1:1 and about 2:1.

16. A magnet as claimed in claim 1 wherein said working space extends entirely around said poles, whereby a physician can have access to a patient disposed in the gap from all locations around the gap.

17. A magnet as claimed in claim 1 or claim 16 wherein said working space is at least about 5.5 feet high and at least about 2 feet wide, whereby a physician can work in a standing position adjacent the gap.

18. A magnet as claimed in claim 1 wherein said working space within said frame is equipped as an operating room, whereby the magnet provides an MRI operating room.

19. A magnet as claimed in claim 1 further comprising shimming means for directing magnetic flux passing through said gap so as to promote magnetic field uniformity in said gap.

20. A magnet as claimed in claim 19 wherein said shimming means includes means for defining magnetic flux paths of different reluctances in different locations relative to said polar axis.

21. A magnet as claimed in claim 20 wherein said means for defining flux paths of different reluctances includes shim rings in said poles adjacent the distal ends thereof.

22. A magnet as claimed in claim 21 wherein said shim rings include a ferromagnetic edge ring at the periphery of each said pole.

23. A magnet as claimed in claim 19 wherein each said pole includes a pole tip defining the distal end of the pole and a pole stem extending from the proximal end of the pole to said pole tip, said flux source is arranged to direct flux in a forward direction through each said pole and said shimming means includes stem bucking magnets surrounding said pole stems, said stem bucking magnets providing flux directed in a reverse direction opposite to said forward direction.

24. A magnet as claimed in claim 1 wherein said flux source includes a pair of coils encircling said poles.

25. A magnet as claimed in claim 24 wherein each of said coils is a resistive coil.

26. A magnet as claimed in claim 24 wherein each of said coils is a superconducting coil.

27. A magnet as claimed in claim 26 wherein each said superconducting coil is superconducting at temperatures up to about 77° K.

28. A magnet as claimed in claim 24 wherein each said coil encircles the associated one of said poles over at least the majority of the axial extent of such pole.

29. A magnet as claimed in claim 24 wherein said polar axis is generally vertical and wherein one of said coils is disposed beneath said working space.

30. A magnet as claimed in claim 29 wherein the other one of said coils is disposed above said working space.

31. A magnet as claimed in claim 1 wherein said flux source includes a permanent magnet.

32. A magnet as claimed in claim 1 wherein said gap distance is at least about 17½ inches.

33. A magnet as claimed in claim 32 wherein said gap distance is at least about 3 feet or more.

34. A magnet as claimed in claim 1 wherein said flux source is adapted to provide a field strength of at least 1 kilogauss in said gap.

35. A magnet as claimed in claim 34 wherein said flux source is adapted to provide a field strength of at least 3 kilogauss in said gap.

36. A magnet as claimed in claim 1 including a plurality of enclosing structures including walls, a floor and a ceiling together defining a room, said distal ends of said poles, said gap and said working space being disposed within said room, at least a part of said frame extending outside of said room.

37. A magnet as claimed in claim 36 wherein said frame forms at least one of said enclosing structures.

38. A magnet as claimed in claim 36 wherein said enclosing structures includes concealment structure at least partially concealing said frame from view from within said room.

39. A magnet as claimed in claim 36 wherein said pole supports are disposed at least partially outside of said room.

40. A magnet as claimed in claim 39 wherein said polar axis is substantially vertical, one of said pole supports extends beneath the floor of said room and the other one of said pole supports extends above the ceiling of said room, and said at least one connecting element extends outside of one or more walls of said room.

41. A magnet as claimed in claim 40 wherein said at least one connecting element includes a plurality of connecting elements disposed along a plurality of walls of said room.

42. A magnet as claimed in claim 41 wherein said connecting elements include a plurality of wall elements at least partially defining a plurality of walls of said room.

43. A magnet as claimed in claim 42 wherein said wall elements include one or more relatively thick columns extending vertically between said pole supports, and one or more plate elements thinner than said columns.

44. A magnet as claimed in claim 42 wherein at least one of said wall elements is of substantially uniform thickness.

45. A magnet as claimed in claim 42 wherein said wall elements define a first pair of opposed walls constituting opposite sides of the room.

46. A magnet as claimed in claim 45 wherein said wall elements include a second pair of opposed walls transverse to said first pair of opposed walls, said first and second pairs of wall elements defining four walls of said room.

47. A magnet as claimed in claim 46 wherein said first pair of opposed walls are spaced at least about 14 feet apart.

48. A magnet as claimed in claim 39 wherein said polar axis is substantially horizontal, one of said pole supports extends outside of one wall of said room and the other one of said pole supports extends outside of another wall of said room.

49. A magnet as claimed in claim 1 wherein said polar axis is substantially vertical and said connecting elements are generally in the form of sectors of a body of revolution about the polar axis.

50. A facility comprising a magnet as claimed in claim 1 and a building structure encompassing said ferromagnetic frame, portions of said building structure being connected to said ferromagnetic frame so that said ferromagnetic frame at least partially supports said building structure.

51. A facility comprising a magnet as claimed in claim 1 and a source of ionizing radiation disposed in or adjacent to said frame so that said frame blocks ionizing radiation from said source.

52. A magnet as claimed in claim 1 wherein said polar axis is substantially horizontal.

53. A magnet as claimed in claim 1 wherein said polar axis is substantially vertical, and wherein said pole supports are disposed at the top and bottom of said frame.

54. A magnet as claimed in claim 1 wherein said polar axis is substantially vertical and said poles are of unequal length, so that said gap has a horizontal medial plane closer to one of said pole supports than to the other one of said pole supports.

55. A magnet as claimed in claim 54 wherein said medial plane is closer to the top pole support than to the bottom pole support.

56. A magnet as claimed in claim 1 wherein said one or more connecting elements is disposed at least about 7 feet from said polar axis.

57. A magnet as claimed in claim 56 wherein said polar axis is substantially vertical and wherein said one or more connecting elements include a pair of connecting elements spaced at least about 14 feet apart.

58. A magnet as claimed in claim 1 wherein each said pole has a generally elliptical tip at its distal end.

59. A magnet for a magnetic resonance imaging apparatus comprising;
  (a) a ferromagnetic frame including:
    (i) a pair of opposed poles extending toward one another along a polar axis, said poles having distal ends defining a gap therebetween, and proximal ends remote from the gap;
    (ii) a pair of pole supports connected to said proximal ends of said poles; and
    (iii) a pair of connecting elements extending alongside of said gap on opposite sides thereof, said connecting elements extending codirectionally with said polar axis said connecting elements being spaced apart from one another in a lengthwise direction transverse to said polar axis; and
  (b) a source of magnetic flux adapted to direct flux so that said flux passes through said gap and returns through said frame, at least those portions of said frame disposed adjacent said gap having thickness in a widthwise dimension transverse to said polar axis and said lengthwise dimension about 48 inches or less.

60. A magnet as claimed in claims 59 wherein said connecting elements are spaced apart from one another in said lengthwise dimension by at least about 7 feet.

61. A magnet as claimed in claim 60 wherein said distal ends of said poles are noncircular so that each said distal end has a long dimension extending in said lengthwise direction and a short dimension extending transverse to said long dimension.

62. A magnet for magnetic resonance imaging comprising:
   (a) a ferromagnetic frame defining an interior and an exterior, said frame further defining a subject-receiving gap within the interior of the frame and a working space within the interior of the frame sufficient to accommodate one or more physicians, whereby a physician in said working space can have access to a patient disposed in said gap; and
   (b) a source of magnetic flux adapted to direct flux so that said flux passes through said gap and returns through said frame.

63. A magnet as claimed in claim 62 wherein said frame includes a pair of ferromagnetic pole supports and at least one ferromagnetic pole projecting toward said gap from at least one of said pole supports.

64. A magnet as claimed in claim 63 wherein said frame includes a pair of ferromagnetic poles projecting from said pole supports to said gap and ferromagnetic structure disposed outside of said working space and providing a flux return path between said poles.

65. A magnetic resonance facility including a magnet as claimed in claim 1 or claim 62 and magnetic resonance imaging apparatus linked to said magnet and utilizing the magnetic field applied by said magnet to provide an image of a subject received in said gap.

66. A facility as claimed in claim 65 further comprising a display visible from within said working space for displaying said image.

67. A facility as claimed in claim 66 further comprising a control input device accessible within said working space for controlling said magnetic resonance imaging apparatus.

68. A magnetic resonance facility as claimed in claim 67 further comprising a pointing device for controlling certain equipment within said magnetic resonance facility.

69. A magnetic resonance facility as claimed in claim 68 further comprising a surgical robot, wherein said pointing device controls said surgical robot.

70. A magnetic resonance facility as claimed in claim 69 wherein said surgical robot includes a surgical probe, said probe being controlled by said pointing device.

71. A magnetic resonance facility as claimed in claim 69 wherein said surgical robot includes a needle, said needle being controlled by said pointing device.

72. A magnetic resonance facility as claimed in claim 69 wherein said surgical robot includes a catheters, said catheter being controlled by said pointing device.

73. A facility as claimed in claim 65 further comprising one or more devices for treating a subject disposed in said gap, said one or more devices be accessible within said working space.

* * * * *

UNITED STATES PATENT AND TRADEMARK OFFICE
CERTIFICATE OF CORRECTION

PATENT NO. : 6,201,394 B1
DATED : March 13, 2001
INVENTOR(S) : Danby et al.

It is certified that error appears in the above-identified patent and that said Letters Patent is hereby corrected as shown below:

Column 2,
Line 52, after "according" insert -- to --.

Column 6,
Line 47, "in" should read -- of --.
After "example" insert -- , --.

Column 8,
Line 41, "SD" should read -- 50 --.
Line 49, delete "a".

Column 9,
Line 65, after "image" delete "-".

Column 10,
Line 32, "carries" should read -- carry --.

Column 11,
Line 7, 4, after "room" insert -- , --.
Line after "seen" delete "-".
Line 2 32, "faraday" should read -- Faraday --.
Line 33, "faraday" should read -- Faraday --.

Column 12,
Line 51, after "kilogauss" insert -- , --.

UNITED STATES PATENT AND TRADEMARK OFFICE
CERTIFICATE OF CORRECTION

PATENT NO. : 6,201,394 B1
DATED : March 13, 2001
INVENTOR(S) : Danby et al.

It is certified that error appears in the above-identified patent and that said Letters Patent is hereby corrected as shown below:

Column 16,
Line 24, after "direction" delete -- , --.

Column 20,
Line 62, after "axis" insert -- , --.

Column 21,
Line 5, "claims" should read -- claim. --

Column 22,
Line 26, "catheters" should read -- catheter --.
Line 30, "be" should read -- being --.

Signed and Sealed this

Thirteenth Day of November, 2001

Attest:

*Nicholas P. Godici*

NICHOLAS P. GODICI
*Attesting Officer*  *Acting Director of the United States Patent and Trademark Office*